US006964199B2

(12) United States Patent
Lee et al.

(10) Patent No.: US 6,964,199 B2
(45) Date of Patent: Nov. 15, 2005

(54) METHODS AND COMPOSITIONS FOR ENHANCED PROTEIN EXPRESSION AND/OR GROWTH OF CULTURED CELLS USING CO-TRANSCRIPTION OF A BCL2 ENCODING NUCLEIC ACID

(75) Inventors: ChiChang Lee, Norristown, PA (US); Xiaomei Shi, Collegeville, PA (US); Celia Ly, Lancaster, PA (US); Gordon Moore, Wayne, PA (US)

(73) Assignee: Cantocor, Inc., Malvern, PA (US)

( * ) Notice: Subject to any disclaimer, the term of this patent is extended or adjusted under 35 U.S.C. 154(b) by 447 days.

(21) Appl. No.: 10/003,632

(22) Filed: Nov. 2, 2001

(65) Prior Publication Data

US 2004/0043028 A1 Mar. 4, 2004

(51) Int. Cl.[7] .................................. G01L 9/14
(52) U.S. Cl. ........................................ 73/735
(58) Field of Search ................. 73/305, 313, 317, 73/319, 735, 753, 427; 340/870.09, 870.16, 870.38, 612, 618, 623, 624, 620

(56) References Cited

FOREIGN PATENT DOCUMENTS

JP          9183983          5/1997

OTHER PUBLICATIONS

E. Suzuki, "Establishing apoptosis resistant cell lines for improving protein productivity of cell culture", Cypotechnology, vol. 23, 1997, pp. 55–59, XP 001009825.

Database WPI week 9735, Derwent Publications Ltd., London, GB, An 1997–380167 XP002208597.

N. Kim et al., "Overexpression of blcl–2 inhibits sodium butyrate–induced apoptosis in Chinese hamster ovary cells resulting in enhanced humanized antibody production.", Biotechnology and Bioengineering, vol. 71, No. 3, 2000, pp. 184–193, XP002208594, New York NY.

B. Tey et al.: "Influence of bcl–2 on cell death during the cultivation of a Chinese hamster ovary cell line expressing a chimeric antibody." Biotechnology and Bioengineering, vol. 6, No. 1, Apr. 5, 2000, pp. 31–43, XP002208595, New York, NY.

N. Simpson et al, "Prevention of hybridoma cell death by bcl–2 during suboptimal culture conditions." Biotechnology and Bioengineering, vol. 54; No. 1, 1997, pp. 1–16, XP002208596.

D. Fassnacht et al:, "Influence of bcl–w on antibody productivity in high cell density perfusion cultures of hybridoma." Cytotechnolgoy, vol. 30, No. 1–3, 1999, pp. 95–105, XP001009822.

International Search Report for application No. PCT/US01/45563 dated Aug. 18, 2002.

Primary Examiner—William Oen

(57) ABSTRACT

The present invention in the field of biotechnology, provides methods and compositions for providing enhanced growth of, and/or protein production from, cultured mammalian host cells used for the production of commercially useful amounts of expressed proteins, by the use of at least one Bcl2 encoding nucleic acid provided or transcribed in the host cell.

37 Claims, 15 Drawing Sheets

Viability in SFM w/o Primatone & Albumin

Total Cell Density in SFM w/o Primatone & Albumin

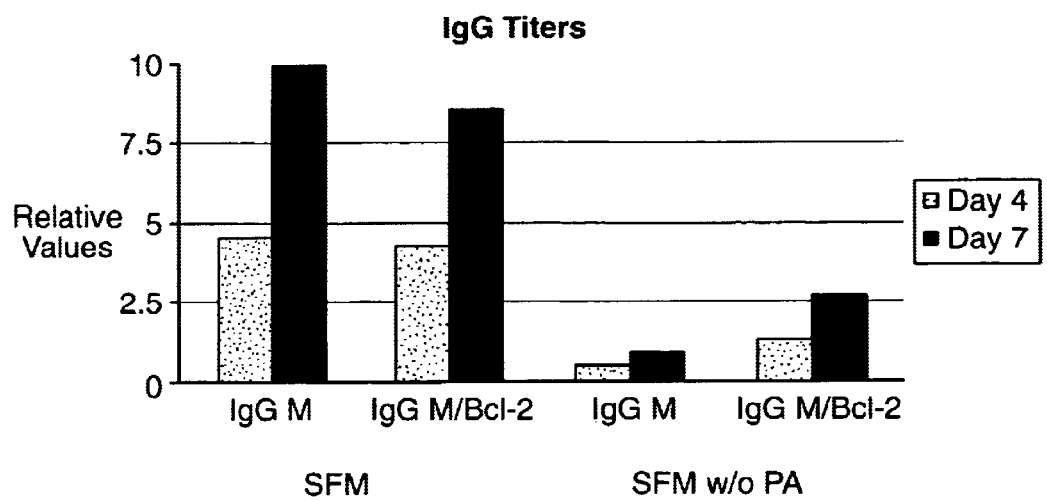
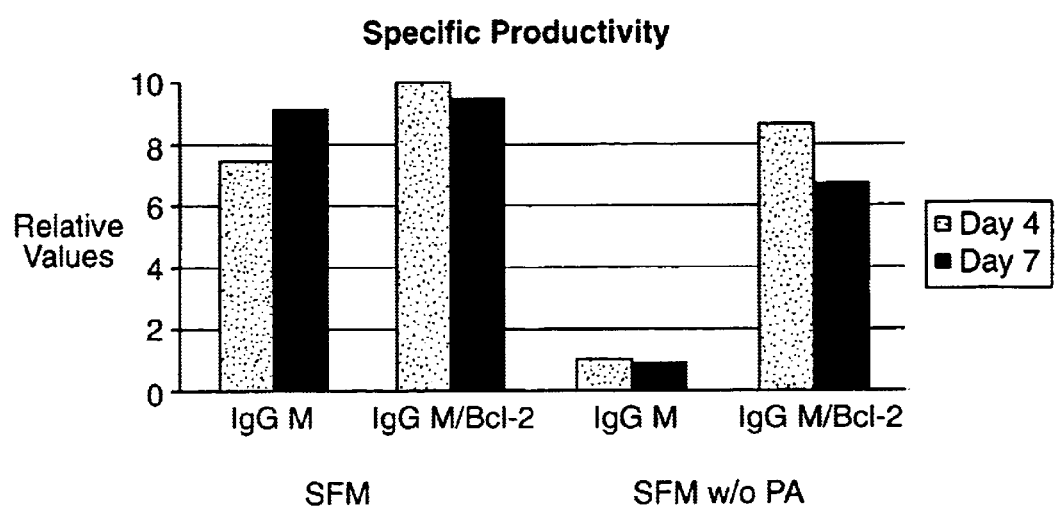

FIG. 10

METHODS AND COMPOSITIONS FOR ENHANCED PROTEIN EXPRESSION AND/OR GROWTH OF CULTURED CELLS USING CO-TRANSCRIPTION OF A BCL2 ENCODING NUCLEIC ACID

FIELD OF THE INVENTION

The present invention in the field of biotechnology, relates to methods and compositions for providing enhanced growth of, and/or protein production from, cultured mammalian host cells used for the production of commercially useful amounts of expressed proteins, by the use of at least one Bcl2 encoding nucleic acid provided or transcribed in the host cell.

BACKGROUND OF THE INVENTION

Current mammalian cell culture techniques provide limited expression levels of proteins, such as therapeutic or diagnostic proteins, including immunoglobulins and fragments thereof. Such cultures require expensive and complex fermentors, media, culture conditions and highly engineered cell lines.

Bovine serum is commonly used in mammalian cell culture to promote cell growth and protein production. Since serum is expensive, non-defined animal materials such as primatone and albumin have been used as serum replacements. However, the quality of these non-defined animal proteins varies from batch to batch and consistent cell growth in these media is difficult to achieve. Moreover, pathogens such as prions and viruses have been identified as potential infectious agents (Balter, M. 2000, Kozak et al. 1996) that may reside in those animal derived products. Many regulations now strongly address these concerns about using serum or non-defined animal proteins in mammalian cells.

To support the growth of animal cells, a variety of components are essential to be included in the culture media. For example, glutamine and glucose are basic energy sources that support animal cell growth. Breakdown of these compounds provides resources for energy-generating pathways, the TCA cycle and glycolysis. The byproducts of these pathways are also the building blocks or sources for bio polymer synthesis (Petch and Bulter 1994). In addition, vitamins, amino acids and growth factors are also essential for robust cell growth by either supressing the cascade of the suicide pathway known as apoptosis or by promoting the progression of the cell cycle so that cells may replicate (Franek F. 1994, Murakami et al. 1982, Mastrangelo et al. 1999, Xie and Wang, 1996, Muhamed Al-Rubeai 1998).

Accordingly, there is also a need to provide improvements that enhance the effectiveness of cell culture and/or production of heterologous proteins in commercially useful amounts.

SUMMARY OF INVENTION

The present invention provides enhanced protein expression in mammalian cell culture using the co-transcription, co-translation or co-expression of at least one Bcl2 related proteins. Such proteins and encoding nucleic acid are well known in the art. The present invention provides the discovery that expression of heterologous proteins in cultured mammalian cells can be enhanced by the use of Bcl2 related protein encoding nucleic acid in the host cells that are used for heterologous protein expression. The enhanced protein expression is qualtitative or quantititative and gives the commercial utility of higher yields of expressed protein and/or comparable or enhanced yields using less robust media.

The present invention also provides methods that enhance the effects of known or other media formulations and methods by the use of cell lines that express at least one Bcl2 encoding nucleic acid. Such media provide certain compounds, amino acids, lipids, carbohydrates, trace elements and/or vitamins that provide a chemically defined media that excludes the use of non-defined animal derived raw materials (e.g., but not limited to, primatone, albumin and Excyte, as well as other similar materials derived from serum or other animal derived proteins or products). Such media compositions and formulations of the present invention allow the growth of myeloma and other cell cultures to provide commercially useful amounts of the desired proteins expressed in such cell cultures.

Accordingly the present invention provides methods, host cells and vectors that enhance the expression of proteins and/or antibodies or antibody fragments or antibody fusion proteins using cell culture media, formulations and methods of making and using thereof, as well as proteins provided therefrom. The present invention provides methods for enhanced expression of at least one protein from mammalian cells that co-express, co-transcribe and/or co-tranlate at least one Bcl2 encoding nucleic acid, wherein the protein is expressed in enhanced amounts over the lack of use of at least one Bcl2 encoding nucleic acid, or where less robust media is needed to express the same or enhanced levels of proteins as compared to more robust media. Thus, the present invention provides one or more advantages of enhanced quantitative or qualitative protein production, commercially suitability, cost-effectiveness, and/or which pose reduced regulatory concerns for proteins produced in cell lines grown therein.

DESCRIPTION OF THE DRAWINGS

FIGS. 8A–B are graphical representations showing day 4 and day 7 IgG titers in SFM complete medium and primatone and albumin depleted SFM for the IgG M and IgG M/Bcl-2 cell lines. T25 flasks were inoculated at 0.1×10^6 cells/ml. (8A) IgG titers on day 4 and 7; (8B) IgG specific productivity on day 4 and 7.

FIG. 10 is a graphical representation showing seventeen day Fed-Batch experiment of IgG R and IgG R/hBCL-2 cell lines in SFM complete medium. Spinner flasks were seeded at 0.4×10^6 cells/mL. IgG R/hBCL-2 maintains higher viability longer and total production is higher. Total density reached 7×10^6 cells/mL for IgG R and 4×10^6 cells/mL for the hBCL-2 line. Viable density reached 3×10^6 cells/mL for both cell lines.

DETAILED DESCRIPTION OF THE INVENTION

Figure 1:
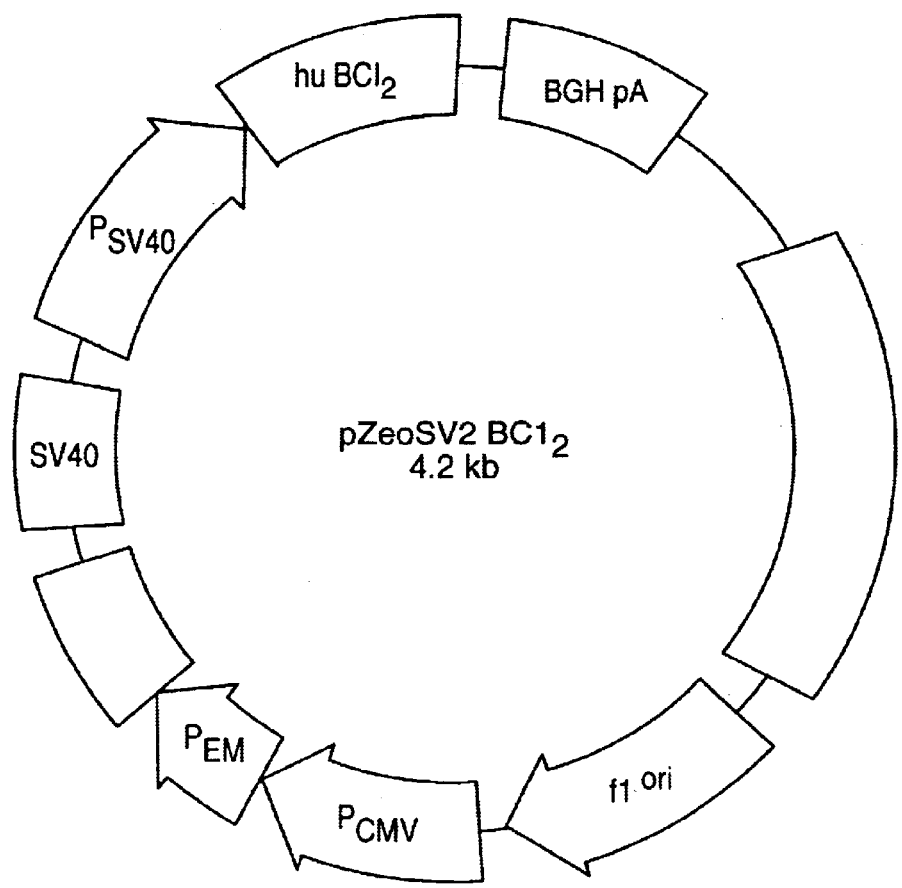
FIG. 1: A vector map shows that a 0.9 kb human Bcl2 gene was excised from pB4 (ATCC 79804) by EcoR1 and cloned into EcoR1 site of pZeoSV2(+'). Selection was done at Zeocin concentration of 50 ug/ml in low salt agar or Broth (Invitrogen). Orientation of insert was determined by several restriction enzyme digestions and then confirmed by DNA sequencing.

The present invention in the field of biotechnology, provides methods and compositions for providing enhanced growth of, and/or protein production from, cultured mammalian host cells used for the production of commercially useful amounts of expressed proteins, by the use of at least one Bcl2 encoding nucleic acid provided or transcribed in the host cell.

The present invention uses known mammalian expression nucleic acid, vectors, regulatory sequences, host cells and the like to enhance protein production using the co-transcription, co-translation or co-expression of at least one Bcl2 related protein encoding nucleic acid, as well known in the art.

Nucleic Acid Molecules

Using the information provided herein, such as the nucleotide sequences encoding at least 10–100% of the contiguous amino acids of at least one of SEQ ID NOS:1, 2, 3, 4, 5, 6, 7, 8, 9, 10, 11, 12, 13, 14, specified fragments, variants or consensus sequences thereof, or a deposited vector comprising at least one of these sequences, a nucleic acid molecule of the present invention encoding at least one Bcl2 related protein or specified portion or variant can be obtained using methods described herein or as known in the art.

Nucleic acid molecules of the present invention can be in the form of RNA, such as mRNA, hnRNA, tRNA or any other form, or in the form of DNA, including, but not limited to, cDNA and genomic DNA obtained by cloning or produced synthetically, or any combinations thereof. The DNA can be triple-stranded, double-stranded or single-stranded, or any combination thereof. Any portion of at least one strand of the DNA or RNA can be the coding strand, also known as the sense strand, or it can be the non-coding strand, also referred to as the anti-sense strand.

Isolated nucleic acid molecules of the present invention encoding a heterologous protein of interest where the protein is an immunoglobulin can include nucleic acid molecules encoding immunoglobulin components comprising an open reading frame (ORF), optionally with one or more introns, e.g., but not limited to, at least one specified portion of at least one CDR, as CDR1, CDR2 and/or CDR3 of at least one heavy chain or light chain; nucleic acid molecules optionally comprising the coding sequence for a Bcl2 related protein, heterologous protein or antibody or fragment, coding for the heavy and light chain variable regions comprising the HC and LC CDRs as presented above, respectively; nucleic acid molecules comprising the coding sequence for a Bcl2 related protein, heterologous protein or antibody or specified portion or variant; and nucleic acid molecules which comprise a nucleotide sequence substantially different from those described above but which, due to the degeneracy of the genetic code, still encode at least one antibody as described herein and/or as known in the art. Of course, the genetic code is well known in the art. Thus, it would be routine for one skilled in the art to generate such degenerate nucleic acid variants that code for specifica Bcl2 related protein, heterologous protein or antibody or specified portion or variants of the present invention. See, e.g., Ausubel, et al., supra, and such nucleic acid variants are included in the present invention.

As indicated herein, nucleic acid molecules of the present invention which comprise a nucleic acid encoding at least one Bcl2 related protein and at least one heterologous protein or antibody or specified portion or variant can include, but are not limited to, those encoding the amino acid sequence of a Bcl2 related protein, heterologous protein or antibody fragment, by itself; the coding sequence for the entire antibody or a portion thereof; the coding sequence for a Bcl2 related protein, heterologous protein or antibody, fragment or portion, as well as additional sequences, such as the coding sequence of at least one signal leader or fusion peptide, with or without the aforementioned additional coding sequences, such as at least one intron, together with additional, non-coding sequences, including but not limited to, non-coding 5' and 3' sequences, such as the transcribed, non-translated sequences that play a role in transcription, mRNA processing, including splicing and polyadenylation signals (for example—ribosome binding and stability of mRNA); an additional coding sequence that codes for additional amino acids, such as those that provide additional functionalities. Thus, the sequence encoding a Bcl2 related protein, heterologous protein or antibody or specified portion or variant can be fused to a marker sequence, such as a sequence encoding a peptide that facilitates purification of the fused antibody or specified portion or variant comprising a Bcl2 related protein, heterologous protein or antibody fragment or portion.

Polynucleotides Which Selectively Hybridize to a Polynucleotide as Described Herein The present invention provides isolated nucleic acids that hybridize under selective hybridization conditions to a polynucleotide encoding Bcl2 related proteins disclosed herein, e.g., at least one of SEQ ID NOS:1, 2, 3, 4, 5, 6, 7, 8, 9, 10, 11 or others disclosed herein or known in the art. Thus, the polynucleotides of this embodiment can be used for isolating, detecting, and/or quantifying nucleic acids comprising such polynucleotides. For example, polynucleotides of the present invention can be used to identify, isolate, or amplify partial or full-length clones in a deposited library. In some embodiments, the polynucleotides are genomic or cDNA sequences isolated, or otherwise complementary to, a cDNA from a human or mammalian nucleic acid library.

Preferably, the cDNA library comprises at least 80% full-length sequences, preferably at least 85% or 90% full-length sequences, and more preferably at least 95% full-length sequences. The cDNA libraries can be normalized to increase the representation of rare sequences. Low or moderate stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% sequence identity and can be employed to identify orthologous or paralogous sequences.

Optionally, polynucleotides of this invention will encode at least a portion of a Bcl2 related protein, heterologous protein or antibody or specified portion or variant encoded by the polynucleotides described herein. The polynucleotides of this invention embrace nucleic acid sequences that can be employed for selective hybridization to a polynucleotide encodinga Bcl2 related protein, heterologous protein or antibody or specified portion or variant of the present invention. See, e.g., Ausubel, supra; Colligan, supra, each entirely incorporated herein by reference.

Construction of Nucleic Acids

The isolated nucleic acids of the present invention can be made using (a) recombinant methods, (b) synthetic techniques, (c) purification techniques, or combinations thereof, as well-known in the art.

The nucleic acids can conveniently comprise sequences in addition to a polynucleotide of the present invention. For example, a multi-cloning site comprising one or more endonuclease restriction sites can be inserted into the nucleic acid to aid in isolation of the polynucleotide. Also, translatable sequences can be inserted to aid in the isolation of the translated polynucleotide of the present invention. For example, a hexa-histidine marker sequence provides a convenient means to purify the proteins of the present invention. The nucleic acid of the present invention—excluding the coding sequence—is optionally a vector, adapter, or linker for cloning and/or expression of a polynucleotide of the present invention.

Additional sequences can be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known in the art. (See, e.g., Ausubel, supra; or Sambrook, supra)

Recombinant Methods for Constructing Nucleic Acids

The isolated nucleic acid compositions of this invention, such as RNA, cDNA, genomic DNA, or any combination thereof, can be obtained from biological sources using any number of cloning methodologies known to those of skill in the art. In some embodiments, oligonucleotide probes that selectively hybridize, under stringent conditions, to the polynucleotides of the present invention are used to identify the desired sequence in a cDNA or genomic DNA library. The isolation of RNA, and construction of cDNA and genomic libraries, is well known to those of ordinary skill in the art. (See, e.g., Ausubel, supra; or Sambrook, supra)

Nucleic Acid Screening and Isolation Methods

A cDNA or genomic library can be screened using a probe based upon the sequence of a polynucleotide of the present invention, such as those disclosed herein. Probes can be used to hybridize with genomic DNA or cDNA sequences to isolate homologous genes in the same or different organisms. Those of skill in the art will appreciate that various degrees of stringency of hybridization can be employed in the assay; and either the hybridization or the wash medium can be stringent. As the conditions for hybridization become more stringent, there must be a greater degree of complementarity between the probe and the target for duplex formation to occur. The degree of stringency can be controlled by one or more of temperature, ionic strength, pH and the presence of a partially denaturing solvent such as formamide. For example, the stringency of hybridization is conveniently varied by changing the polarity of the reactant solution through, for example, manipulation of the concentration of formamide within the range of 0% to 50%. The degree of complementarity (sequence identity) required for detectable binding will vary in accordance with the stringency of the hybridization medium and/or wash medium. The degree of complementarity will optimally be 100%, or 90–100%, or any range or value therein. However, it should be understood that minor sequence variations in the probes and primers can be compensated for by reducing the stringency of the hybridization and/or wash medium.

Methods of amplification of RNA or DNA are well known in the art and can be used according to the present invention without undue experimentation, based on the teaching and guidance presented herein.

Known methods of DNA or RNA amplification include, but are not limited to, polymerase chain reaction (PCR) and related amplification processes (see, e.g., U.S. Pat. Nos. 4,683,195, 4,683,202, 4,800,159, 4,965,188, to Mullis, et al.; U.S. Pat. Nos. 4,795,699 and 4,921,794 to Tabor, et al; U.S. Pat. No. 5,142,033 to Innis; U.S. Pat. No. 5,122,464 to Wilson, et al.; U.S. Pat. No. 5,091,310 to Innis; U.S. Pat. No. 5,066,584 to Gyllensten, et al; U.S. Pat. No. 4,889,818 to Gelfand, et al; U.S. Pat. No. 4,994,370 to Silver, et al; U.S. Pat. No. 4,766,067 to Biswas; U.S. Pat. No. 4,656,134 to Ringold) and RNA mediated amplification that uses anti-sense RNA to the target sequence as a template for double-stranded DNA synthesis (U.S. Pat. No. 5,130,238 to Malek, et al, with the tradename NASBA), the entire contents of which references are incorporated herein by reference. (See, e.g., Ausubel, supra; or Sambrook, supra.)

For instance, polymerase chain reaction (PCR) technology can be used to amplify the sequences of polynucleotides of the present invention and related genes directly from genomic DNA or cDNA libraries. PCR and other in vitro amplification methods can also be useful, for example, to clone nucleic acid sequences that code for proteins to be expressed, to make nucleic acids to use as probes for detecting the presence of the desired mRNA in samples, for nucleic acid sequencing, or for other purposes. Examples of techniques sufficient to direct persons of skill through in vitro amplification methods are found in Berger, supra, Sambrook, supra, and Ausubel, supra, as well as Mullis, et al., U.S. Pat. No. 4,683,202 (1987); and Innis, et al., PCR Protocols A Guide to Methods and Applications, Eds., Academic Press Inc., San Diego, Calif. (1990). Commercially available kits for genomic PCR amplification are known in the art. See, e.g., Advantage-GC Genomic PCR Kit (Clontech). The T4 gene 32 protein (Boehringer Mannheim) can be used to improve yield of long PCR products.

Synthetic Methods for Constructing Nucleic Acids

The isolated nucleic acids of the present invention can also be prepared by direct chemical synthesis by known methods (see, e.g., Ausubel, et al., supra). Chemical synthesis generally produces a single-stranded oligonucleotide, which can be converted into double-stranded DNA by hybridization with a complementary sequence, or by polymerization with a DNA polymerase using the single strand as a template. One of skill in the art will recognize that while chemical synthesis of DNA can be limited to sequences of about 100 or more bases, longer sequences can be obtained by the ligation of shorter sequences.

Recombinant Expression Cassettes

The present invention further provides recombinant expression cassettes comprising a nucleic acid of the present invention. A nucleic acid sequence of the present invention, for example a cDNA or a genomic sequence encoding a Bcl2 related protein, heterologous protein or antibody or specified portion or variant of the present invention, can be used to construct a recombinant expression cassette that can be introduced into at least one desired host cell. A recombinant expression cassette will typically comprise a polynucleotide of the present invention operably linked to transcriptional initiation regulatory sequences that will direct the transcription of the polynucleotide in the intended host cell.

Both heterologous and non-heterologous (i.e., endogenous) promoters can be employed to direct expression of the nucleic acids of the present invention. These promoters can also be used, for example, in recombinant expression cassettes to drive expression of antisense nucleic acids to reduce, increase, or alter content and/or composition in a desired tissue.

In some embodiments, isolated nucleic acids that serve as promoter, enhancer, or other elements can be introduced in the appropriate position (upstream, downstream or in intron) of a non-heterologous form of a polynucleotide of the present invention so as to up or down regulate expression of a polynucleotide of the present invention. For example, endogenous promoters can be altered in vivo or in vitro by mutation, deletion and/or substitution.

A polynucleotide of the present invention can be expressed in either sense or anti-sense orientation as desired. It will be appreciated that control of gene expression in either sense or anti-sense orientation can have a direct impact on the observable characteristics.

Another method of suppression is sense suppression. Introduction of nucleic acid configured in the sense orientation has been shown to be an effective means by which to block the transcription of target genes.

A variety of cross-linking agents, alkylating agents and radical generating species as pendant groups on polynucleotides of the present invention can be used to bind, label, detect and/or cleave nucleic acids. Knorre, et al., Biochimie 67:785–789 (1985); Vlassov, et al., Nucleic Acids Res. 14:4065–4076 (1986); Iverson and Dervan, J. Am. Chem. Soc. 109:1241–1243 (1987); Meyer, et al., J. Am. Chem. Soc. 111:8517–8519 (1989); Lee, et al., Biochemistry 27:3197–3203 (1988); Home, et al., J. Am. Chem. Soc. 112:2435–2437 (1990); Webb and Matteucci, J. Am. Chem. Soc. 108:2764–2765 (1986); Nucleic Acids Res. 14:7661–7674 (1986); Feteritz, et al., J. Am. Chem. Soc. 113:4000 (1991). Various compounds to bind, detect, label, and/or cleave nucleic acids are known in the art. See, for example, U.S. Pat. Nos. 5,543,507; 5,672,593; 5,484,908; 5,256,648; and 5,681,941, each entirely incorporated herein by reference.

Vectors and Host Cells

The present invention also relates to vectors that include isolated nucleic acid molecules of the present invention, host cells that are genetically engineered with the recombinant vectors, and the production using at least one Bcl2 related protein encoding nucleic acid of at least one heterologous protein or antibody or specified portion or variant by recombinant techniques, as is well known in the art. See, e.g., Sambrook, et al., supra; Ausubel, et al., supra, each entirely incorporated herein by reference.

The polynucleotides can optionally be joined to a vector containing a selectable marker for propagation in a host. Generally, a plasmid vector is introduced in a precipitate, such as a calcium phosphate precipitate, or in a complex with a charged lipid. If the vector is a virus, it can be packaged in vitro using an appropriate packaging cell line and then transduced into host cells.

The DNA insert should be operatively linked to an appropriate promoter. The expression constructs will further contain sites for transcription initiation, termination and, in the transcribed region, a ribosome binding site for translation. The coding portion of the mature transcripts expressed by the constructs will preferably include a translation initiating at the beginning and a termination codon (e.g., UAA, UGA or UAG) appropriately positioned at the end of the mRNA to be translated, with UAA and UAG preferred for mammalian or eukaryotic cell expression.

Expression vectors will preferably but optionally include at least one selectable marker. Such markers include, e.g., but not limited to, methotrexate (MTX), dihydrofolate reductase (DHFR, U.S. Pat. Nos. 4,399,216; 4,634,665; 4,656,134; 4,956,288; 5,149,636; 5,179,017, ampicillin, neomycin (G418), mycophenolic acid, or glutamine synthetase (GS, U.S. Pat. Nos. 5,122,464; 5,770,359; 5,827, 739) resistance for eukaryotic cell culture, and tetracycline or ampicillin resistance genes for culturing in *E. coli* and other bacteria or prokaryotics (the above patents are entirely incorporated hereby by reference). Appropriate culture mediums and conditions for the above-described host cells are known in the art. Suitable vectors will be readily apparent to the skilled artisan. Introduction of a vector construct into a host cell can be effected by calcium phosphate transfection, DEAE-dextran mediated transfection, cationic lipid-mediated transfection, electroporation, transduction, infection or other known methods. Such methods are described in the art, such as Sambrook, supra, Chapters 1–4 and 16–18; Ausubel, supra, Chapters 1, 9, 13, 15, 16.

At least one heterologous protein, antibody or specified portion or variant of the present invention can be expressed in a modified form, such as a fusion protein, and can include not only secretion signals, but also additional heterologous functional regions. For instance, a region of additional amino acids, particularly charged amino acids, can be added to the N-terminus of a protein, antibody or specified portion or variant to improve stability and persistence in the host cell, during purification, or during subsequent handling and storage. Also, peptide moieties can be added to a protein, antibody or specified portion or variant of the present invention to facilitate purification. Such regions can be removed prior to final preparation of a protein, antibody or at least one fragment thereof. Such methods are described in many standard laboratory manuals, such as Sambrook, supra, Chapters 17.29–17.42 and 18.1–18.74; Ausubel, supra, Chapters 16, 17 and 18.

Those of ordinary skill in the art are knowledgeable in the numerous expression systems available for expression of a nucleic acid encoding a protein of the present invention.

Alternatively, nucleic acids of the present invention can be expressed in a host cell by turning on (by manipulation) in a host cell that contains endogenous DNA encoding a Bcl2 related protein, a heterologous protein or antibody or specified portion or variant of the present invention. Such methods are well known in the art, e.g., as described in U.S. Pat. Nos. 5,580,734, 5,641,670, 5,733,746, and 5,733,761, entirely incorporated herein by reference.

Illustrative of cell cultures useful for the production of the antibodies, specified portions or variants thereof, are mammalian cells. Mammalian cell systems often will be in the form of monolayers of cells although mammalian cell suspensions or bioreactors can also be used. A number of suitable host cell lines capable of expressing intact glycosylated proteins have been developed in the art, and include the COS-1 (e.g., ATCC CRL 1650), COS-7 (e.g., ATCC CRL-1651), HEK293, BHK21 (e.g., ATCC CRL-10), CHO (e.g., ATCC CRL 1610) and BSC-1 (e.g., ATCC CRL-26) cell lines, Cos-7 cells, CHO cells, hep G2 cells, P3X63Ag8.653, SP2/0-Ag14, 293 cells, HeLa cells and the like, which are readily available from, for example, American Type Culture Collection, Manassas, Va. Preferred host cells include cells of lymphoid origin such as myeloma and lymphoma cells. Particularly preferred host cells are P3X63Ag8.653 cells (ATCC Accession Number CRL-1580) and SP2/0-Ag14 cells (ATCC Accession Number CRL-1851). In a particularly preferred embodiment, the recombinant cell is a P3X63Ab8.653 or a SP2/0-Ag14 cell.

Expression vectors for these cells can include one or more of the following expression control sequences, such as, but not limited to an origin of replication; a promoter (e.g., late or early SV40 promoters, the CMV promoter (U.S. Pat. Nos. 5,168,062; 5,385,839), an HSV tk promoter, a pgk (phosphoglycerate kinase) promoter, an EF-1 alpha promoter (U.S. Pat. No. 5,266,491), at least one human immunoglobulin promoter; an enhancer, and/or processing information sites, such as ribosome binding sites, RNA splice sites, polyadenylation sites (e.g., an SV40 large T Ag poly A addition site), and transcriptional terminator sequences. See, e.g., Ausubel et al., supra; Sambrook, et al., supra. Other cells useful for production of nucleic acids or proteins of the present invention are known and/or available, for instance, from the American Type Culture Collection Catalogue of Cell Lines and Hybridomas (www.atcc.org) or other known or commercial sources.

When eukaryotic host cells are employed, polyadenlyation or transcription terminator sequences are typically incorporated into the vector. An example of a terminator sequence is the polyadenlyation sequence from the bovine growth hormone gene. Sequences for accurate splicing of the transcript can also be included. An example of a splicing sequence is the VP1 intron from SV40 (Sprague, et al., J. Virol. 45:773–781 (1983)). Additionally, gene sequences to control replication in the host cell can be incorporated into the vector, as known in the art.

Purification of a Heterologous Protein, Antibody or Specified Portion or Variant Thereof A heterologous protein, antibody or specified portion or variant can be recovered and purified from recombinant cell cultures by well-known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be employed for purification. See e.g., Colligan, Current Protocols in Immunology, or Current Protocols in Protein Science, John Wiley & Sons, NY, N.Y., (1997–2000), e.g., Chapters 1, 4, 6, 8, 9, 10, each entirely incorporated herein by reference.

Proteins, antibodies or specified portions or variants of the present invention include naturally purified products, products of chemical synthetic procedures, and products produced by recombinant techniques from a eukaryotic host, including, for example, yeast, higher plant, insect and mammalian cells. Depending upon the host employed in a recombinant production procedure, the antibody or specified portion or variant of the present invention can be glycosylated or can be non-glycosylated, with glycosylated preferred. Such methods are described in many standard laboratory manuals, such as Sambrook, supra, Sections 17.37–17.42; Ausubel, supra, Chapters 10, 12, 13, 16, 18 and 20, Colligan, Protein Science, supra, Chapters 12–14, all entirely incorporated herein by reference.

Bcl2 Related Proteins, Heterologous Proteins, Antibodies, Fragments and/or Variants The isolated antibodies of the present invention comprise a Bcl2 related protein, heterologous protein or antibody or specified portion or variant encoded by any one of the polynucleotides of the present invention as discussed more fully herein, or any isolated or prepared antibody or specified portion or variant thereof.

Preferably, the human antibody or antigen-binding fragment binds a specific human protein and, thereby substantially neutralizes the biological activity of the protein. A heterologous protein or antibody, or specified portion or variant thereof, that partially or preferably substantially agonizes, antagonizes or modulates at least one biological activity of at least one target protein or fragment can bind the protein or fragment and thereby modulate activities mediated through the binding of the protein to a protein receptor or through other protein-dependent or mediated mechanisms. As used herein, the term "neutralizing antibody"

refers to a heterologous protein or antibody that can inhibit a protein-dependent activity by about 20–120%, preferably by at least about 60, 70, 80, 90, 91, 92, 93, 94, 95, 96, 97, 98, 99, 100% or more depending on the assay. The capacity of a heterologous protein, antibody or specified portion or variant to modulate a heterologous protein-dependent activity is preferably assessed by at least one suitable antibody or protein assay, as described herein and/or as known in the art. A human antibody or specified portion or variant of the invention can be of any class (IgG, IgA, IgM, etc.) or isotype and can comprise a kappa or lambda light chain. In one embodiment, the human antibody or specified portion or variant comprises an IgG heavy chain or defined fragment, for example, at least one of isotypes, IgG1, IgG2, IgG3 or IgG4. Antibodies of this type can be prepared by employing a transgenic mouse or other transgenic non-human mammal comprising at least one human light chain (e.g., Ig, Ig and Ig (e.g., 1, 2, 3, 4) transgenes as described herein and/or as known in the art. In another embodiment, the anti-human protein human antibody or specified portion or variant thereof comprises an IgG1 heavy chain and a IgG1 light chain.

At least one antibody or specified portion or variant of the invention binds at least one specified epitope specific to at least one heterologous protein, subunit, fragment, portion or any combination thereof. The at least one epitope can comprise at least one antibody binding region that comprises at least one portion of said protein, which epitope is preferably comprised of at least one extracellular, soluble, hydrophillic, external or cytoplasmic portion of said protein. The at least one specified epitope can comprise any combination of at least one amino acid sequence of at least 1–3 amino acids to the entire specified portion of at least one contiguous amino acids of the sequences selected from the group consisting of any 3–50 amino acids of the heterologous protein.

Generally, the human antibody or antigen-binding fragment of the present invention will comprise an antigen-binding region that comprises at least one human complementarity determining region (CDR1, CDR2 and CDR3) or variant of at least one heavy chain variable region and at least one human complementarity determining region (CDR1, CDR2 and CDR3) or variant of at least one light chain variable region. As a non-limiting example, the antibody or antigen-binding portion or variant can comprise at least one of the heavy chain CDR3, and/or a light chain CDR3. In a particular embodiment, the antibody or antigen-binding fragment can have an antigen-binding region that comprises at least a portion of at least one heavy chain CDR (i.e., CDR1, CDR2 and/or CDR3) having the amino acid sequence of the corresponding CDRs 1, 2 and/or 3. In another particular embodiment, the antibody or antigen-binding portion or variant can have an antigen-binding region that comprises at least a portion of at least one light chain CDR (i.e., CDR1, CDR2 and/or CDR3) having the amino acid sequence of the corresponding CDRs 1, 2 and/or 3. In a preferred embodiment the three heavy chain CDRs and the three light chain CDRs of the antibody or antigen-binding fragment have the amino acid sequence of the corresponding CDR. Such antibodies can be prepared by chemically joining together the various portions (e.g., CDRs, framework) of the antibody using conventional techniques, by preparing and expressing a (i.e., one or more) nucleic acid molecule that encodes the antibody using conventional techniques of recombinant DNA technology or by using any other suitable method.

The anti-human human antibody can comprise at least one of a heavy or light chain variable region having a defined amino acid sequence. For example, in a preferred embodiment, the human anti-human antibody comprises at least one of at least one heavy chain variable region. Human antibodies that bind to human heterologous proteins and that comprise a defined heavy or light chain variable region can be prepared using suitable methods, such as phage display (Katsube, Y., et al., *Int J Mol. Med*, 1(5):863–868 (1998)) or methods that employ transgenic animals, as known in the art and/or as described herein. For example, a transgenic mouse, comprising a functionally rearranged human immunoglobulin heavy chain transgene and a transgene comprising DNA from a human immunoglobulin light chain locus that can undergo functional rearrangement, can be immunized with human protein or a fragment thereof to elicit the production of antibodies. If desired, the antibody producing cells can be isolated and hybridomas or other immortalized antibody-producing cells can be prepared as described herein and/or as known in the art. Alternatively, the antibody, specified portion or variant can be expressed using the encoding nucleic acid or portion thereof in a suitable host cell.

The invention also relates to antibodies, antigen-binding fragments, immunoglobulin chains and CDRs comprising amino acids in a sequence that is substantially the same as an amino acid sequence described herein. Preferably, such antibodies or antigen-binding fragments and antibodies comprising such chains or CDRs can bind human protein with high affinity (e.g., $K_D$ less than or equal to about $10^{-9}$ M). Amino acid sequences that are substantially the same as the sequences described herein include sequences comprising conservative amino acid substitutions, as well as amino acid deletions and/or insertions. A conservative amino acid substitution refers to the replacement of a first amino acid by a second amino acid that has chemical and/or physical properties (e.g, charge, structure, polarity, hydrophobicity/hydrophilicity) that are similar to those of the first amino acid. Conservative substitutions include replacement of one amino acid by another within the following groups: lysine (K), arginine (R) and histidine (H); aspartate (D) and glutamate (E); asparagine (N), glutamine (Q), serine (S), threonine (T), tyrosine (Y), K, R, H, D and E; alanine (A), valine (V), leucine (L), isoleucine (I), proline (P), phenylalanine (F), tryptophan (W), methionine (M), cysteine (C) and glycine (G); F, W and Y; C, S and T.

Amino Acid Codes

The amino acids that make up protein antibodies or specified portions or variants of the present invention are often abbreviated. The amino acid designations can be indicated by designating the amino acid by its single letter code, its three letter code, name, or three nucleotide codon(s) as is well understood in the art (see Alberts, B., et al., Molecular Biology of The Cell, Third Ed., Garland Publishing, Inc., New York, 1994):

| SINGLE LETTER CODE | THREE LETTER CODE | NAME | THREE NUCLEOTIDE CODON(S) |
|---|---|---|---|
| A | Ala | Alanine | GCA, GCC, GCG, GCU |
| C | Cys | Cysteine | UGC, UGU |
| D | Asp | Aspartic acid | GAC, GAU |
| E | Glu | Glutamic acid | GAA, GAG |
| F | Phe | Phenylanine | UUC, UUU |
| G | Gly | Glycine | GGA, GGC, GGG, GGU |
| H | His | Histidine | CAC, CAU |
| I | Ile | Isoleucine | AUA, AUC, AUU |

-continued

| SINGLE LETTER CODE | THREE LETTER CODE | NAME | THREE NUCLEOTIDE CODON(S) |
|---|---|---|---|
| K | Lys | Lysine | AAA, AAG |
| L | Leu | Leucine | UUA, UUG, CUA, CUC, CUG, CUU |
| M | Met | Methionine | AUG |
| N | Asn | Asparagine | AAC, AAU |
| P | Pro | Proline | CCA, CCC, CCG, CCU |
| Q | Gln | Glutamine | CAA, CAG |
| R | Arg | Arginine | AGA, AGG, CGA, CGC, CGG, CGU |
| S | Ser | Serine | AGC, AGU, UCA, UCC, UCG, UCU |
| T | Thr | Threonine | ACA, ACC, ACG, ACU |
| V | Val | Valine | GUA, GUC, GUG, GUU |
| W | Trp | Tryptophan | UGG |
| Y | Tyr | Tyrosine | UAC, UAU |

A heterologous protein, antibody or specified portion or variant of the present invention can include one or more amino acid substitutions, deletions or additions, either from natural mutations or human manipulation, as specified herein.

Of course, the number of amino acid substitutions a skilled artisan would make depends on many factors, including those described above. Generally speaking, the number of amino acid substitutions, insertions or deletions for any given polypeptide will not be more than 40, 30, 20, 19, 18, 17, 16, 15, 14, 13, 12, 11, 10, 9, 8, 7, 6, 5, 4, 3, 2, 1, such as 1–30 or any range or value therein, as specified herein.

Amino acids in a Heterologous protein or antibody or specified portion or variant of the present invention that are essential for function can be identified by methods known in the art, such as site-directed mutagenesis or alanine-scanning mutagenesis (e.g., Ausubel, supra, Chapters 8, 15; Cunningham and Wells, Science 244:1081–1085 (1989)). The latter procedure introduces single alanine mutations at every residue in the molecule. The resulting mutant molecules are then tested for biological activity, such as, but not limited to at least one protein neutralizing activity. Sites that are critical for antibody or specified portion or variant binding can also be identified by structural analysis such as crystallization, nuclear magnetic resonance or photoaffinity labeling (Smith, et al., J. Mol. Biol. 224:899–904 (1992) and de Vos, et al., Science 255:306–312 (1992)).

Heterologous protein or antibodies or specified portions or variants of the present invention can include, but are not limited to, at least one portion, sequence or combination selected from 5—5 contiguous amino acids of SEQ ID NO:7, 5–17 contiguous amino acids of SEQ ID NO:8, 5–17 contiguous amino acids of SEQ ID NO:9, 5–11 contiguous amino acids of SEQ ID NO:10, 5–7 contiguous amino acids of SEQ ID NO:11; 5–10 contiguous amino acids of SEQ ID NO:12; 5–115 contiguous amino acids of SEQ ID NO:13; 5–109 contiguous amino acids of SEQ ID NO:14.

Non-limiting variants that can enhance or maintain at least one of the listed activities include, but are not limited to, any of the above polypeptides, further comprising at least one mutation corresponding to at least one substitution selected from the group consisting of (a) 1Ile, 1Phe, 3Leu, 8Ser, 10Lys, 17Asp; (b) 4Val, 5Ala, 5Gly, 9Tyr, 7Tyr; 28Ile, 43Asn, 50Iln, 51Met, 52Leu, 57Ser, 59Lys, 60Ser, 66Asp, 70Val, 75Pro, 78Ala, 80Phe, 94Phe, 102Val, 103Ala, 103Gly, 107Y, of at least one of SEQ ID NOS:7, 8, 9, 10, 11, 12, 13, 14.

A(n) Bcl2 related protein, heterologous protein or antibody, or specified portion or variant can further optionally comprise a polypeptide of at least one of 90–100% of the contiguous amino acids for a Bcl2 related protein of at least one of SEQ ID NOS:1, 2, 3, 4, 5, 6, 7, 8, 9, 10, 11, 12, 13, 14 and 15.

In one embodiment, the amino acid sequence of a Bcl2 related protein has about 90–100% identity (i.e., 90, 91, 92, 93, 94, 95, 96, 97, 98, 99, 100 or any range or value therein) to the amino acid sequence of the corresponding chain of at least one of SEQ ID NOS:1, 2, 3, 4, 5, 6, 7, 8, 9, 10, 11, 12, 13, 14.

In another aspect, the invention relates to human heterologous proteins or antibodies and antigen-binding fragments, as described herein, which are modified by the covalent attachment of an organic moiety. Such modification can produce a heterologous protein or antibody or antigen-binding fragment with improved pharmacokinetic properties (e.g., increased in vivo serum half-life). The organic moiety can be a linear or branched hydrophilic polymeric group, fatty acid group, or fatty acid ester group. In particular embodiments, the hydrophilic polymeric group can have a molecular weight of about 800 to about 120,000 Daltons and can be a polyalkane glycol (e.g., polyethylene glycol (PEG), polypropylene glycol (PPG)), carbohydrate polymer, amino acid polymer or polyvinyl pyrolidone, and the fatty acid or fatty acid ester group can comprise from about eight to about forty carbon atoms.

The modified proteins, antibodies and antigen-binding fragments of the invention can comprise one or more organic moieties that are covalently bonded, directly or indirectly, to the antibody or specified portion or variant. Each organic moiety that is bonded to heterologous protein or antibody or antigen-binding fragment of the invention can independently be a hydrophilic polymeric group, a fatty acid group or a fatty acid ester group. As used herein, the term "fatty acid" encompasses mono-carboxylic acids and di-carboxylic acids. A "hydrophilic polymeric group," as the term is used herein, refers to an organic polymer that is more soluble in water than in octane. For example, polylysine is more soluble in water than in octane. Thus, a Bcl2 related protein, heterologous protein or antibody modified by the covalent attachment of polylysine is encompassed by the invention. Hydrophilic polymers suitable for modifying antibodies of the invention can be linear or branched and include, for example, polyalkane glycols (e.g., PEG, monomethoxy-polyethylene glycol (mPEG), PPG and the like), carbohydrates (e.g., dextran, cellulose, oligosaccharides, polysaccharides and the like), polymers of hydrophilic amino acids (e.g., polylysine, polyarginine, polyaspartate and the like), polyalkane oxides (e.g., polyethylene oxide, polypropylene oxide and the like) and polyvinyl pyrolidone. Preferably, the hydrophilic polymer that modifies the antibody of the invention has a molecular weight of about 800 to about 150,000 Daltons as a separate molecular entity. For example $PEG_{5000}$ and $PEG_{20,000}$, wherein the subscript is the average molecular weight of the polymer in Daltons, can be used.

The hydrophilic polymeric group can be substituted with one to about six alkyl, fatty acid or fatty acid ester groups. Hydrophilic polymers that are substituted with a fatty acid or fatty acid ester group can be prepared by employing suitable methods. For example, a polymer comprising an amine group can be coupled to a carboxylate of the fatty acid or fatty acid ester, and an activated carboxylate (e.g., activated with N,N-carbonyl diimidazole) on a fatty acid or fatty acid ester can be coupled to a hydroxyl group on a polymer.

Fatty acids and fatty acid esters suitable for modifying antibodies of the invention can be saturated or can contain one or more units of unsaturation. Fatty acids that are suitable for modifying antibodies of the invention include, for example, n-dodecanoate ($C_{12}$, laurate), n-tetradecanoate ($C_{14}$, myristate), n-octadecanoate ($C_{18}$, stearate), n-eicosanoate ($C_{20}$, arachidate), n-docosanoate ($C_{22}$, behenate), n-triacontanoate ($C_{30}$), n-tetracontanoate ($C_{40}$), cis- 9-octadecanoate ($C_{18}$, oleate), all cis-5,8,11,14-eicosatetraenoate ($C_{20}$, arachidonate), octanedioic acid, tetradecanedioic acid, octadecanedioic acid, docosanedioic acid, and the like. Suitable fatty acid esters include monoesters of dicarboxylic acids that comprise a linear or branched lower alkyl group. The lower alkyl group can comprise from one to about twelve, preferably one to about six, carbon atoms.

The modified human proteins, antibodies and antigen-binding fragments can be prepared using suitable methods, such as by reaction with one or more modifying agents. A "modifying agent" as the term is used herein, refers to a suitable organic group (e.g., hydrophilic polymer, a fatty acid, a fatty acid ester) that comprises an activating group. An "activating group" is a chemical moiety or functional group that can, under appropriate conditions, react with a second chemical group thereby forming a covalent bond between the modifying agent and the second chemical group. For example, amine-reactive activating groups include electrophilic groups such as tosylate, mesylate, halo (chloro, bromo, fluoro, iodo), N-hydroxysuccinimidyl esters (NHS), and the like. Activating groups that can react with thiols include, for example, maleimide, iodoacetyl, acrylolyl, pyridyl disulfides, 5-thiol-2-nitrobenzoic acid thiol (TNB-thiol), and the like. An aldehyde functional group can be coupled to amine- or hydrazide-containing molecules, and an azide group can react with a trivalent phosphorous group to form phosphoramidate or phosphorimide linkages. Suitable methods to introduce activating groups into molecules are known in the art (see for example, Hermanson, G. T., *Bioconjugate Techniques*, Academic Press: San Diego, Calif. (1996)). An activating group can be bonded directly to the organic group (e.g., hydrophilic polymer, fatty acid, fatty acid ester), or through a linker moiety, for example a divalent $C_1$–$C_{12}$ group wherein one or more carbon atoms can be replaced by a heteroatom such as oxygen, nitrogen or sulfur. Suitable linker moieties include, for example, tetraethylene glycol, —($CH_2$)$_3$—, —NH—($CH_2$)$_6$—NH—, —($CH_2$)$_2$—NH— and —$CH_2$—O—$CH_2$—$CH_2$—O—$CH_2$—$CH_2$—O—$CH$—NH—. Modifying agents that comprise a linker moiety can be produced, for example, by reacting a mono-Boc-alkyldiamine (e.g., mono-Boc-ethylenediamine, mono-Boc-diaminohexane) with a fatty acid in the presence of 1-ethyl-3-(3-dimethylaminopropyl) carbodiimide (EDC) to form an amide bond between the free amine and the fatty acid carboxylate. The Boc protecting group can be removed from the product by treatment with trifluoroacetic acid (TFA) to expose a primary amine that can be coupled to another carboxylate as described, or can be reacted with maleic anhydride and the resulting product cyclized to produce an activated maleimido derivative of the fatty acid. (See, for example, Thompson, et al., WO 92/16221 the entire teachings of which are incorporated herein by reference.)

The modified proteins or antibodies of the invention can be produced by reacting an human protein, antibody or antigen-binding fragment with a modifying agent. For example, the organic moieties can be bonded to the antibody in a non-site specific manner by employing an amine-reactive modifying agent, for example, an NHS ester of PEG. Modified human antibodies or antigen-binding fragments can also be prepared by reducing disulfide bonds (e.g., intra-chain disulfide bonds) of a Bcl2 related protein, heterologous protein or antibody or antigen-binding fragment. The reduced antibody or antigen-binding fragment can then be reacted with a thiol-reactive modifying agent to produce the modified antibody of the invention. Modified human antibodies and antigen-binding fragments comprising an organic moiety that is bonded to specific sites of heterologous protein or antibody or specified portion or variant of the present invention can be prepared using suitable methods, such as reverse proteolysis (Fisch et al., *Bioconjugate Chem.*, 3:147–153 (1992); Werlen et al., *Bioconjugate Chem.*, 5:411–417 (1994); Kumaran et al., *Protein Sci.* 6(10):2233–2241 (1997); Itoh et al., *Bioorg. Chem.*, 24(1): 59–68 (1996); Capellas et al., *Biotechnol. Bioeng.*, 56(4) :456–463 (1997)), and the methods described in Hermanson, G. T., *Bioconjugate Techniques*, Academic Press: San Diego, Calif. (1996).

Heterologous Protein, Antibody or Specified Portion or Variant Compositions

The present invention also provides at least one Heterologous protein or antibody or specified portion or variant composition comprising at least one, at least two, at least three, at least four, at least five, at least six or more Heterologous protein or antibodies or specified portions or variants thereof, as described herein and/or as known in the art that are provided in a non-naturally occurring composition, mixture or form. Such compositions comprise non-naturally occurring compositions comprising at least one or two full length, C- and/or N-terminally deleted variants, domains, fragments, or specified variants, of the Heterologous protein or antibody amino acid sequence selected from the group consisting of 90–100% of the contiguous amino acids of specified fragments, domains or variants thereof. Preferred compositions include at least one or two full length, fragments, domains or variants. Further preferred compositions comprise 40–99% of at least one of 90–100% of protein, specified fragments, domains or variants thereof. Such composition percentages are by weight, volume, concentration, molarity, or molality as liquid or dry solutions, mixtures, suspension, emulsions or colloids, as known in the art or as described herein.

Heterologous protein or antibody or specified portion or variant compositions of the present invention can further comprise at least one of any suitable auxiliary, such as, but not limited to, diluent, binder, stabilizer, buffers, salts, lipophilic solvents, preservative, adjuvant or the like. Pharmaceutically acceptable auxiliaries are preferred. Non-limiting examples of, and methods of preparing such sterile solutions are well known in the art, such as, but limited to, Gennaro, Ed., *Remington's Pharmaceutical Sciences*, 18$^{th}$ Edition, Mack Publishing Co. (Easton, Pa.) 1990. Pharmaceutically acceptable carriers can be routinely selected that are suitable for the mode of administration, solubility and/or stability of the composition as well known in the art or as described herein.

Pharmaceutical excipients and additives useful in the present composition include but are not limited to proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1–99.99% by weight or volume. Exemplary protein excipients include serum albumin such as human serum albumin (HSA), recombinant human albumin (rHA), gelatin, casein, and the like. Representative amino acid/antibody or specified portion or variant components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. One preferred amino acid is glycine.

Carbohydrate excipients suitable for use in the invention include, for example, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), myoinositol and the like. Preferred carbohydrate excipients for use in the present invention are mannitol, trehalose, and raffinose.

Protein compositions can also include a buffer or a pH adjusting agent; typically, the buffer is a salt prepared from an organic acid or base. Representative buffers include organic acid salts such as salts of citric acid, ascorbic acid, gluconic acid, carbonic acid, tartaric acid, succinic acid, acetic acid, or phthalic acid; Tris, tromethamine hydrochloride, or phosphate buffers. Preferred buffers for use in the present compositions are organic acid salts such as citrate.

Additionally, the Heterologous protein or antibody or specified portion or variant compositions of the invention can include polymeric excipients/additives such as polyvinylpyrrolidones, ficolls (a polymeric sugar), dextrates (e.g., cyclodextrins, such as 2-hydroxypropyl-β-cyclodextrin), polyethylene glycols, flavoring agents, antimicrobial agents, sweeteners, antioxidants, antistatic agents, surfactants (e.g., polysorbates such as "TWEEN 20" and "TWEEN 80"), lipids (e.g., phospholipids, fatty acids), steroids (e.g., cholesterol), and chelating agents (e.g., EDTA).

These and additional known pharmaceutical excipients and/or additives suitable for use in the compositions according to the invention are known in the art, e.g., as listed in "Remington: The Science & Practice of Pharmacy", 19$^{th}$ ed., Williams & Williams, (1995), and in the "Physician's Desk Reference", 52$^{nd}$ ed., Medical Economics, Montvale, N.J. (1998), the disclosures of which are entirely incorporated herein by reference. Preferred carrier or excipient materials are carbohydrates (e.g., saccharides and alditols) and buffers (e.g., citrate) or polymeric agents.

Formulations

As noted above, the invention provides for stable formulations, which is preferably a phosphate buffer with saline or a chosen salt, as well as preserved solutions and formulations containing a preservative as well as multi-use preserved formulations suitable for pharmaceutical or veterinary use, comprising at least one Heterologous protein or antibody or specified portion or variant in a pharmaceutically acceptable formulation. Preserved formulations contain at least one known preservative or optionally selected from the group consisting of at least one phenol, m-cresol, p-cresol, o-cresol, chlorocresol, benzyl alcohol, phenylmercuric nitrite, phenoxyethanol, formaldehyde, chlorobutanol, magnesium chloride (e.g., hexahydrate), alkylparaben (methyl, ethyl, propyl, butyl and the like), benzalkonium chloride, benzethonium chloride, sodium dehydroacetate and thimerosal, or mixtures thereof in an aqueous diluent. Any suitable concentration or mixture can be used as known in the art, such as 0.001–5%, or any range or value therein, such as, but not limited to 0.001, 0.003, 0.005, 0.009, 0.01, 0.02, 0.03, 0.05, 0.09, 0.1, 0.2, 0.3, 0.4., 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.3, 4.5, 4.6, 4.7, 4.8, 4.9, or any range or value therein. Non-limiting examples include, no preservative, 0.1–2% m-cresol (e.g., 0.2, 0.3, 0.4, 0.5, 0.9, 1.0%), 0.1–3% benzyl alcohol (e.g., 0.5, 0.9, 1.1., 1.5, 1.9, 2.0, 2.5%), 0.001–0.5% thimerosal (e.g., 0.005, 0.01), 0.001–2.0% phenol (e.g., 0.05, 0.25, 0.28, 0.5, 0.9, 1.0%), 0.0005–1.0% alkylparaben(s) (e.g., 0.00075, 0.0009, 0.001, 0.002, 0.005, 0.0075, 0.009, 0.01, 0.02, 0.05, 0.075, 0.09, 0.1, 0.2, 0.3, 0.5, 0.75, 0.9, 1.0%), and the like.

As noted above, the invention provides an article of manufacture, comprising packaging material and at least one vial comprising a solution of at least one Heterologous protein or antibody or specified portion or variant with the prescribed buffers and/or preservatives, optionally in an aqueous diluent, wherein said packaging material comprises a label that indicates that such solution can be held over a period of 1, 2, 3, 4, 5, 6, 9, 12, 18, 20, 24, 30, 36, 40, 48, 54, 60, 66, 72 hours or greater. The invention further comprises an article of manufacture, comprising packaging material, a first vial comprising lyophilized at least one Heterologous protein or antibody or specified portion or variant, and a second vial comprising an aqueous diluent of prescribed buffer or preservative, wherein said packaging material comprises a label that instructs a patient to reconstitute the at least one Heterologous protein or antibody or specified portion or variant in the aqueous diluent to form a solution that can be held over a period of twenty-four hours or greater.

The at least one protein or antibody or specified portion or variant used in accordance with the present invention can be produced by recombinant means, including from mammalian cell or transgenic preparations, or can be purified from other biological sources, as described herein or as known in the art.

The range of at least one heterologous protein or antibody or specified portion or variant in the product of the present invention includes amounts yielding upon reconstitution, if in a wet/dry system, concentrations from about 1.0 μg/ml to about 1000 mg/ml, although lower and higher concentrations are operable and are dependent on the intended delivery vehicle, e.g., solution formulations will differ from transdermal patch, pulmonary, transmucosal, or osmotic or micro pump methods.

Preferably, the aqueous diluent optionally further comprises a pharmaceutically acceptable preservative. Preferred preservatives include those selected from the group consisting of phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal, or mixtures thereof. The concentration of preservative used in the formulation is a concentration sufficient to yield an antimicrobial effect. Such concentrations are dependent on the preservative selected and are readily determined by the skilled artisan.

Other excipients, e.g. isotonicity agents, buffers, antioxidants, preservative enhancers, can be optionally and preferably added to the diluent. An isotonicity agent, such as glycerin, is commonly used at known concentrations. A physiologically tolerated buffer is preferably added to provide improved pH control. The formulations can cover a wide range of pHs, such as from about pH 4 to about pH 10, and preferred ranges from about pH 5 to about pH 9, and a most preferred range of about 6.0 to about 8.0. Preferably the formulations of the present invention have pH between about 6.8 and about 7.8. Preferred buffers include phosphate buffers, most preferably sodium phosphate, particularly phosphate buffered saline (PBS).

Other additives, such as a pharmaceutically acceptable solubilizers like Tween 20 (polyoxyethylene (20) sorbitan monolaurate), Tween 40 (polyoxyethylene (20) sorbitan monopalmitate), Tween 80 (polyoxyethylene (20) sorbitan monooleate), Pluronic F68 (polyoxyethylene polyoxypropylene block copolymers), and PEG (polyethylene glycol) or non-ionic surfactants such as polysorbate 20 or 80 or poloxamer 184 or 188, Pluronic® polyls, other block co-polymers, and chelators such as EDTA and EGTA can optionally be added to the formulations or compositions to reduce aggregation. These additives are particularly useful if a pump or plastic container is used to administer the formulation. The presence of pharmaceutically acceptable surfactant mitigates the propensity for the protein to aggregate.

The formulations of the present invention can be prepared by a process which comprises mixing at least one Heterologous protein or antibody or specified portion or variant and a preservative selected from the group consisting of phenol, m-cresol, p-cresol, o-cresol, chlorocresol, benzyl alcohol, alkylparaben, (methyl, ethyl, propyl, butyl and the like), benzalkonium chloride, benzethonium chloride, sodium dehydroacetate and thimerosal or mixtures thereof in an aqueous diluent. Mixing the at least one Heterologous protein or antibody or specified portion or variant and preservative in an aqueous diluent is carried out using conventional dissolution and mixing procedures. To prepare a suitable formulation, for example, a measured amount of at least one Heterologous protein or antibody or specified portion or variant in buffered solution is combined with the desired preservative in a buffered solution in quantities sufficient to provide the protein and preservative at the desired concentrations. Variations of this process would be recognized by one of ordinary skill in the art. For example, the order the components are added, whether additional additives are used, the temperature and pH at which the formulation is prepared, are all factors that may be optimized for the concentration and means of administration used.

The claimed formulations can be provided to patients as clear solutions or as dual vials comprising a vial of lyophilized at least one Heterologous protein or antibody or specified portion or variant that is reconstituted with a second vial containing water, a preservative and/or excipients, preferably a phosphate buffer and/or saline and a chosen salt, in an aqueous diluent. Either a single solution vial or dual vial requiring reconstitution can be reused multiple times and can suffice for a single or multiple cycles of patient treatment and thus can provide a more convenient treatment regimen than currently available.

The present claimed articles of manufacture are useful for administration over a period of immediately to twenty-four hours or greater. Accordingly, the presently claimed articles of manufacture offer significant advantages to the patient. Formulations of the invention can optionally be safely stored at temperatures of from about 2 to about 40° C. and retain the biologically activity of the protein for extended periods of time, thus, allowing a package label indicating that the solution can be held and/or used over a period of 6, 12, 18, 24, 36, 48, 72, or 96 hours or greater. If preserved diluent is used, such label can include use up to 1–12 months, one-half, one and a half, and/or two years.

The solutions of at least one heterologous protein or antibody or specified portion or variant in the invention can be prepared by a process that comprises mixing at least one antibody or specified portion or variant in an aqueous diluent. Mixing is carried out using conventional dissolution and mixing procedures. To prepare a suitable diluent, for example, a measured amount of at least one antibody or specified portion or variant in water or buffer is combined in quantities sufficient to provide the protein and optionally a preservative or buffer at the desired concentrations. Variations of this process would be recognized by one of ordinary skill in the art. For example, the order the components are added, whether additional additives are used, the temperature and pH at which the formulation is prepared, are all factors that may be optimized for the concentration and means of administration used.

The claimed products can be provided to patients as clear solutions or as dual vials comprising a vial of lyophilized at least one Heterologous protein or antibody or specified portion or variant that is reconstituted with a second vial containing the aqueous diluent. Either a single solution vial or dual vial requiring reconstitution can be reused multiple times and can suffice for a single or multiple cycles of patient treatment and thus provides a more convenient treatment regimen than currently available.

The claimed products can be provided indirectly to patients by providing to pharmacies, clinics, or other such institutions and facilities, clear solutions or dual vials comprising a vial of lyophilized at least one Heterologous protein or antibody or specified portion or variant that is reconstituted with a second vial containing the aqueous diluent. The clear solution in this case can be up to one liter or even larger in size, providing a large reservoir from which smaller portions of the at least one antibody or specified portion or variant solution can be retrieved one or multiple times for transfer into smaller vials and provided by the pharmacy or clinic to their customers and/or patients.

Recognized devices comprising these single vial systems include those pen-injector devices for delivery of a solution such as Humaject®, NovoPen®, B-D®Pen, AutoPen®, and OptiPen®. Recognized devices comprising a dual vial system include those pen-injector systems for reconstituting a lyophilized drug in a cartridge for delivery of the reconstituted solution such as the HumatroPen®.

The products presently claimed include packaging material. The packaging material provides, in addition to the information required by the regulatory agencies, the conditions under which the product can be used. The packaging material of the present invention provides instructions to the patient to reconstitute the at least one Heterologous protein or antibody or specified portion or variant in the aqueous diluent to form a solution and to use the solution over a period of 2–24 hours or greater for the two vial, wet/dry, product. For the single vial, solution product, the label indicates that such solution can be used over a period of 2–24 hours or greater. The presently claimed products are useful for human pharmaceutical product use.

The formulations of the present invention can be prepared by a process that comprises mixing at least one Heterologous protein or antibody or specified portion or variant and a selected buffer, preferably a phosphate buffer containing saline or a chosen salt. Mixing the at least one antibody or specified portion or variant and buffer in an aqueous diluent is carried out using conventional dissolution and mixing procedures. To prepare a suitable formulation, for example, a measured amount of at least one antibody or specified portion or variant in water or buffer is combined with the desired buffering agent in water in quantities sufficient to provide the protein and buffer at the desired concentrations.

Variations of this process would be recognized by one of ordinary skill in the art. For example, the order the components are added, whether additional additives are used, the temperature and pH at which the formulation is prepared, are all factors that can be optimized for the concentration and means of administration used.

The claimed stable or preserved formulations can be provided to patients as clear solutions or as dual vials comprising a vial of lyophilized at least one heterologous protein or antibody or specified portion or variant that is reconstituted with a second vial containing a preservative or buffer and excipients in an aqueous diluent. Either a single solution vial or dual vial requiring reconstitution can be reused multiple times and can suffice for a single or multiple cycles of patient treatment and thus provides a more convenient treatment regimen than currently available.

At least one heterologous protein or antibody or specified portion or variant in either the stable or preserved formulations or solutions described herein, can be administered to a patient in accordance with the present invention via a variety of delivery methods including SC or IM injection; transdermal, pulmonary, transmucosal, implant, osmotic pump, cartridge, micro pump, or other means appreciated by the skilled artisan, as well-known in the art.

Suitable cell lines that can be used according to the present invention include any transformed or immortalized mammalian cell line. Such cell lines can include myeloma cell lines, such as Sp2/0, NSO, NS1, CHO, P3X63Ag8.653 cells (ATCC Accession Number CRL-1580) and SP2/0-Ag14 cells (ATCC Accession Number CRL-1851), COS-1 (e.g., ATCC CRL 1650), COS-7 (e.g., ATCC CRL-1651), HEK293, BHK21 (e.g., ATCC CRL-10), CHO (e.g., ATCC CRL 1610) and BSC-1 (e.g., ATCC CRL-26) cell lines. CHO cells, HepG2 cells, P3X63Ag8.653, 293 cells, HeLa cells and the like, or any cells derived therefrom, including cell fusions of the above, such as to protein producing cells, such as B-cells, antibody producing cells, isolated or cloned spleen or lymph node cells, and the like. A preferred cell line is derived from Sp2/0 is designated C463A, as described herein.

Cell lines, such as those presented herein, can be adapted to a media according to the present invention, using known techniques and/or as described herein. Such methods can take from 1–30 days, or up to several months, depending on the particular cell line and media formulation used. However, adaption of mammalian cells having at least one Bcl2 encoding nucleic acid for growth in media of the present invention is unexpectedly found to occur in significantly shorter times that known defined or undefined media.

At least one method or composition of the present invention is unexpectedly discovered to provide at least one of several advantages, including at least one of: (1) supporting improved or robust growth and protein or antibody production from various mammalian cell lines; (2) facilitated adaptation for protein producing cell lines; and/or (3) cost-effective media components, as compared to known components, which do not need to be and/or are not included.

The present invention can use any one of suitable culture technologies, such as but not limited to culture dishes, culture plates, culture bottles, suspension culture, bioreactors, perfusion type bioreactors, mammalian cell fermentation culture, or any other suitable type of cell culture.

A media formulation used according to the present invention can include at least one of specified buffers, salts, carbohydrates, vitamins, proteins, amino acids, lipids, trace elements, minerals, and the like as described herein in combination with what is known in the art.

Non-limiting examples of such buffers and include at least one of MOPES, sodium phosphate, potassium phosphate, HEPES, and the like. Such salts include, but are not limited to sodium chloride, potassium chloride, and the like Such carbohydrates include, but are not limited to, glucose (dextrose), fructose, mannose, galactose, and the like.

Such proteins or amino acids include, but are not limited to, alanine, arginine, asparagine, aspartate, cysteine, cystine, glutamine, glutamate, glycine, histidine, isoleucine, leucine, lysine, methionine, phenylalanine, proline, serine, threonine, tryptophan, tyrosine, valine, INSERT, and salts or other derivatives thereof. Alternatively, such amino acids include at least one of L-amino-n-butyric acid, L-alanine, L-arginine, L-aspartic acid, L-asparagine, L-cysteine, L-citrulline, L-cysteine, D-glucosamine, L-glutamic acid, L-glutamine, L-glycine, L-histidine, hydroxy-L-Proline, L-isoleucine, L-leucine, L-lysine, L-methionine, L-ornithine, L-ornithine, L-phenylalanine, L-proline, L-serine, taurine, L-threonine, L-tryptophan, L-tyrosine, L-valine, and the like, as well as salts, hydrates, hydrides, acids, bases thereof and the like.

Such amounts of buffers include at least one of phosphate and bicarbonate buffers, EDTA, HEPES, MOPES, and the like.

Known serum free hybridoma media that can be used in accordance with present invention include, but are not limited to, e.g., Sigma/Aldrich product numbers S2772, S2897 and S8284 (www.sigma-aldrich.com); similar known serum free media include those from Life Technologies, Rockville, Md. (www.lifetech.com) and JRH Biosciences, Lenexa, Kans. (www.jrhbio.com). For example, known serum free hybridoma cell cultures can include HEPES or MOPS, sodium bicarbonate, L-glutamine, cholesterol, insulin, BSA, transferrin, in addition to other serum free mammalian cell culture components. See, e.g., SIGMA catalog, 1998, pp 1776–1777, 1677–1704, 1715–1755, 1795–1847, entirely incorporated herein by reference. Non-limiting examples of known serum free media that can be modified to provide CDM of the present invention include, but are not limited to, sigma media product numbers S2772, S2897 and S8284, as follows:

| SIGMA Prod. # Component | S 2897 g/L | S 8284 g/L | S2772 g/L |
|---|---|---|---|
| INORGANIC SALTS | | | |
| AlCl3.6H2O | 0.000001 | 0.000001 | 0.000001 |
| NH4VO3 | 0.0000006 | 0.0000006 | 0.0000006 |
| BaCl2 | 0.000002 | 0.000002 | 0.000002 |
| CaCl2.2H2O | 0.0441 | 0.0441 | 0.0441 |
| CoCl2.6H2O | 0.000002 | 0.000002 | 0.000002 |
| CrK(SO4)2 | 0.000001 | 0.000001 | 0.000001 |
| CuSO4.5H2O | 0.0000051 | 0.0000051 | 0.0000051 |
| FeSO4.7H2O | 0.000834 | 0.000834 | 0.000834 |
| GeO2 | 0.0000005 | 0.0000005 | 0.0000005 |
| LiCl | 0.01 | 0.01 | 0.01 |
| MgCl.6H2O | 0.123 | 0.123 | 0.123 |
| MnCl(anhyd) | 0.0000001 | 0.0000001 | 0.0000001 |
| Na2MoO4.2H2O | 0.0000001 | 0.0000001 | 0.0000001 |
| NiNO3.6H2O | 0.0000002 | 0.0000002 | 0.0000002 |
| KBr | 0.0000001 | 0.0000001 | 0.0000001 |
| KCl | 0.224 | 0.224 | 0.224 |
| KI | 0.0000001 | 0.0000001 | 0.0000001 |
| RbCl | 0.00000001 | 0.00000001 | 0.00000001 |
| AgCl | 0.0000000044 | 0.0000000044 | 0.0000000044 |

-continued

| SIGMA Prod. # Component | S 2897 g/L | S 8284 g/L | S2772 g/L |
|---|---|---|---|
| NaHCO3 | — | 2.25 | 2.25 |
| NaCl | 7.599 | 7.599 | 7.599 |
| NaF | 0.000004 | 0.000004 | 0.000004 |
| Na2HPO4(anhyd) | 0.39739 | 0.39739 | 0.39739 |
| Na2SeO3 | 0.00003 | 0.00003 | 0.00003 |
| SnCl2.2H2O | 0.0000001 | 0.0000001 | 0.0000001 |
| TiO2 | 0.000001 | 0.000001 | 0.000001 |
| ZnSO4.7H2O | 0.000863 | 0.000863 | 0.000863 |
| AMINO ACIDS | | | |
| L-Alanine | 0.009 | 0.009 | 0.009 |
| L-Arginine | 0.211 | 0.211 | 0.211 |
| L-Asparagine.H2O | 0.03401 | 0.03401 | 0.03401 |
| L-Aspartic Acid | 0.0133 | 0.0133 | 0.0133 |
| L-Citrulline | 0.005 | 0.005 | 0.005 |
| L-Cysteine.HCl.H2O | 0.035 | 0.035 | 0.035 |
| L-Glutamic Acid | 0.0147 | 0.0147 | 0.0147 |
| L-Glutamine | 0.396 | 0.396 | 0.396 |
| Glycine | 0.00751 | 0.00751 | 0.00751 |
| L-Histidine.HCl.H2O | 0.071 | 0.071 | 0.071 |
| L-Isoleucine | 0.164 | 0.164 | 0.164 |
| L-Leucine | 0.133 | 0.133 | 0.133 |
| L-Lysine.HCl | 0.109 | 0.109 | 0.109 |
| L-Methionine | 0.015 | 0.015 | 0.015 |
| L-Ornithine | 0.008 | 0.008 | 0.008 |
| L-Phenylalanine | 0.055 | 0.055 | 0.055 |

See, e.g., Ham et al., Proc. Natl. Acad. Sci. USA 53:288–193 (1965); Myoken et al., In Vitro 25:477–480 (1989).

More preferably, the media further comprises at least one selected from the group consisting of buffers, salts, carbohydrates, amino acids, lipids, vitamins, co-factors, and the like in suitable form. Suitable media that can be used or modified according to the present invention can include one or more or a combination of Iscove's modified media, Dulbecco's Modified Eagle Medium, Ham's F-12 media, e.g., as provided by SIGMA, LIFE TECHNOLOGIES OR JRH BIOSCIENCES, as listed above. Non-limiting examples, include, but are not limited to:

Iscove's Modified Media: (Sigma I 2510, I 7633, I 2762, I 3390):

| SIGMA Prod. Num. COMPONENT | I 2510, I 7633 g/L | I 2762, I 3390 g/L |
|---|---|---|
| INORG. SALTS | | |
| CaCl2.2H2O | 0.219 | 0.219 |
| MgSO4 (anhyd) | 0.09767 | 0.09767 |
| KCl | 0.33 | 0.33 |
| KNO3 | 0.000076 | 0.000076 |

-continued

| SIGMA Prod. Num. COMPONENT | I 2510, I 7633 g/L | I 2762, I 3390 g/L |
|---|---|---|
| NaHCO3 | — | 3.024 |
| KCl | 4.505 | 4.505 |
| NaH2PO4 (anhyd.) | 0.109 | 0.109 |
| Na2SeO3 | 0.000017 | 0.000017 |
| AMINO ACIDS | | |
| Alanine | 0.025 | 0.025 |
| L-Arginine.HCl | 0.084 | 0.084 |
| L-Asparagine.H$_2$O | 0.0284 | 0.0284 |
| L-Aspartic Acid | 0.03 | 0.03 |
| L-Cystine.2HCl | 0.09124 | 0.09124 |
| L-Glutamic Acid | 0.075 | 0.075 |
| L-Glutamine | 0.584 | — |
| Glycine | 0.03 | 0.03 |
| L-Histidine.HCl.H2O | 0.042 | 0.042 |
| L-Isoleucine | 0.105 | 0.105 |
| L-Leucine | 0.105 | 0.105 |
| L-Lysine.HCl | 0.146 | 0.146 |
| L-Methionine | 0.03 | 0.03 |
| L-Phenylalanine | 0.066 | 0.066 |
| L-Proline | 0.04 | 0.04 |
| L-Serine | 0.042 | 0.042 |
| L-Threonine | 0.095 | 0.095 |
| L-Tryptophan | 0.016 | 0.016 |
| L-Tyrosine.2Na.2H2O | 0.10379 | 0.10379 |
| L-Valine | 0.094 | 0.094 |
| VITAMINS | | |
| D-Biotin | 0.000013 | 0.000013 |
| Choline Chloride | 0.004 | 0.004 |
| Folic Acid | 0.004 | 0.004 |
| myo-Inositol | 0.0072 | 0.0072 |
| Niacinamide | 0.004 | 0.004 |
| D-Pantothenic Acid.½Ca | 0.0004 | 0.004 |
| Pyridoxal.HCl | 0.004 | 0.004 |
| Riboflavin | 0.0004 | 0.0004 |
| Thiamine.HCl | 0.004 | 0.004 |
| Vitamin B12 | 0.000013 | 0.000013 |
| OTHER | | |
| D-Glucose | 4.5 | 4.5 |
| HEPES | 5.958 | 5.958 |
| Phenol Red.Na | 0.016 | 0.016 |
| Pyruvic Acid.Na | 0.11 | 0.11 |
| ADD | | |
| NaHCO3 | 3.024 | — |
| L-Glutamine | — | 0.584 |
| Grams of powder required to prepare 1 L | 17.7 | N/A |

See, e.g., Iscove et al., J. Exp. Med. 147:923–933 (1978); Iscove, et al., Exp. Cell Res. 126:121–126 (1980).

Dulbecco's Modified Eagle's Medium (e.g., Sigma D0422, D 1152, D 2429, D 2554, D2902, D 3656, D 5030, D5280, D5523).

| SIGMA Prod # COMPONENT | D0422 g/L | D1152 g/L | D2429 g/L | D2554 g/L | D2902 g/L | D3656 g/L | D5030 g/L | D5280 g/L | D5523 g/L |
|---|---|---|---|---|---|---|---|---|---|
| INORGANIC SALTS | | | | | | | | | |
| CaCl2.2H2O | 0.265 | 0.265 | 2.65 | 2.65 | 0.265 | 0.265 | 0.265 | 0.265 | 0.265 |
| Fe(NO3)3.9H2O | 0.0001 | 0.0001 | 0.001 | 0.001 | 0.0001 | 0.0001 | 0.0001 | 0.0001 | 0.0001 |

-continued

| SIGMA Prod # COMPONENT | D0422 g/L | D1152 g/L | D2429 g/L | D2554 g/L | D2902 g/L | D3656 g/L | D5030 g/L | D5280 g/L | D5523 g/L |
|---|---|---|---|---|---|---|---|---|---|
| MgSO4 | 0.09767 | 0.09767 | 0.9767 | 0.9767 | 0.09767 | 0.09767 | 0.09767 | 0.09767 | 0.09767 |
| KCl | 0.4 | 0.4 | 4.0 | 4.0 | 0.4 | 0.4 | 0.4 | 0.4 | 0.4 |
| NaHCO3 | 3.7 | — | — | — | — | — | | | |
| NaCl | 6.4 | 4.4 | 64.0 | 64.0 | 6.4 | 6.4 | 6.4 | 6.4 | 6.4 |
| NaH2PO4 | 0.109 | 0.109 | 1.09 | 1.09 | 0.109 | — | 0.109 | 0.109 | 0.109 |
| Succinic Acid | | | | | | | 0.075 | | |
| Sodium Succinate | — | — | — | — | — | — | 0.1 | — |
| AMINO ACIDS | | | | | | | | | |
| L-Arginine.HCl | 0.84 | 0.084 | 0.84 | 0.84 | 0.084 | 0.084 | 0.084 | 0.084 | 0.084 |
| L-Cystine.2HCl | — | 0.0626 | 0.626 | 0.626 | 0.0626 | 0.0626 | 0.0626 | 0.0626 | 0.0626 |
| L-Glutamine | 0.03 | 0.584 | 0.30 | 0.30 | 0.584 | 0.584 | — | — | 0.584 |
| Glycine | 0.042 | 0.030 | 0.42 | 0.42 | 0.030 | 0.030 | 0.030 | 0.030 | 0.030 |
| L-Histidine.HCl.H2O | 0.105 | 0.042 | 1.05 | 1.05 | 0.042 | 0.042 | 0.042 | 0.042 | 0.042 |
| L-Isoleucine | 0.105 | 0.105 | 1.05 | 1.05 | 0.105 | 0.105 | 0.105 | 0.105 | 0.105 |
| L-Leucine | 1.46 | 0.105 | 1.46 | 1.46 | 0.105 | 0.105 | 0.105 | 0.105 | 0.105 |
| L-Lysine.HCl | — | 0.146 | 0.30 | 0.30 | 0.146 | 0.146 | 0.146 | 0.146 | 0.146 |
| L-Methionine | 0.066 | 0.030 | 0.66 | 0.66 | 0.030 | 0.030 | 0.030 | 0.030 | 0.030 |
| L-Phenylalanine | 0.042 | 0.066 | 0.42 | 0.42 | 0.066 | 0.066 | 0.066 | 0.066 | 0.066 |
| L-Serine | 0.095 | 0.042 | 0.95 | 0.95 | 0.042 | 0.042 | 0.042 | 0.042 | 0.042 |
| L-Threonine | 0.016 | 0.095 | 0.16 | 0.16 | 0.095 | 0.095 | 0.095 | 0.095 | 0.095 |
| L-Tryptophan | 0.016 | — | — | 0.016 | 0.016 | 0.016 | 0.016 | 0.016 | |
| L-Tyrosine (free base) | 0.10379 | — | — | 1.0379 | 1.0379 | — | — | 0.072 | — |
| L-Tyrosine.2Na.2H2O | 0.10379 | 0.10379 | 0.10379 | 0.10379 | — | 0.10379 | | | |
| L-Valine | 0.094 | 0.094 | 0.94 | 0.94 | 0.094 | 0.094 | 0.094 | 0.094 | 0.094 |
| VITAMINS | | | | | | | | | |
| Choline Bitartrate | 0.004 | — | 0.04 | 0.04 | — | — | — | 0.0072 | — |
| Choline Chloride | 0.004 | 0.004 | — | — | 0.004 | 0.004 | 0.004 | — | 0.004 |
| Folic Acid | 0.0072 | 0.004 | 0.072 | 0.072 | 0.004 | 0.004 | 0.004 | 0.004 | 0.004 |
| myo-Inositol | 0.004 | 0.0072 | 0.04 | 0.04 | 0.0072 | 0.0072 | 0.0072 | 0.0072 | 0.0072 |
| Niacinamide | 0.004 | 0.004 | 0.04 | 0.04 | 0.004 | 0.004 | 0.004 | 0.004 | 0.004 |
| D-Pantothenic Acid.½Ca | 0.004 | 0.004 | — | — | 0.004 | 0.004 | 0.004 | 0.004 | 0.004 |
| Pyridoxal.HCl | — | 0.004 | 0.04 | 0.04 | 0.004 | 0.004 | 0.004 | 0.004 | 0.004 |
| Pyridoxine.HCl | 0.0004 | — | 0.004 | 0.004 | — | — | — | — | — |
| Riboflavin | 0.004 | 0.0004 | 0.04 | 0.04 | 0.0004 | 0.0004 | 0.0004 | 0.0004 | 0.0004 |
| Thiamine.HCl | 0.004 | 0.004 | 0.004 | 0.004 | 0.004 | 0.004 | 0.004 | 0.004 | 0.004 |
| OTHER | | | | | | | | | |
| D-Glucose | 4.5 | 4.5 | 10.0 | 45.0 | 1.0 | 4.5 | — | 1.0 | — |
| HEPES | — | 5.958 | — | — | — | — | — | — | 0.0159 |
| Phenol Red.Na | 0.0159 | 0.0159 | 0.159 | 0.159 | — | 0.0159 | — | 0.0093 | 0.11 |
| Pyruvic Acid.Na | 0.11 | — | 1.1 | 1.1 | 0.11 | — | — | 0.11 | — |
| ADD | | | | | | | | | |
| Glucose | — | — | — | — | — | 1.0 | — | — | — |

| SIGMA Prod # COMPONENT | D0422 g/L | D1152 g/L | D2429 g/L | D2554 g/L | D2902 g/L | D3656 g/L | D5030 g/L | D5280 g/L | D5523 g/L |
|---|---|---|---|---|---|---|---|---|---|
| L-Glutamine | 0.584 | — | 0.584 | 0.584 | — | — | 0.584 | 0.584 | — |
| L-Cystine.2HCl | — | — | — | — | — | — | — | — | — |
| L-Leucine | | | | | | | | | |
| Lysine.HCl | — | — | — | — | — | — | — | — | — |
| L-Methionine | | | | | | | | | |
| NaHCO3 | — | 3.7 | 3.7 | 3.7 | 3.7 | 3.7 | 3.7 | 3.7 | 3.7 |
| NaH2PO4 | — | — | — | — | — | 0.109 | — | — | — |
| Phenol Red.Na | — | — | — | — | — | 1.0 | — | — | — |
| Pyruvic Acid.Na | — | — | — | — | — | — | — | — | — |
| Grams of powder to prepare 1 L | N/A | 17.4 | N/A | N/A | N/A | N/A | N/A | N/A | 10.0 |

See, e.g., Dulbecco and Freeman, Virology 8:396–397 (1959); Smith et al., J. D., Freeman, G., Vogt, M. and Dulbecco, R. (1960). Virology 12:185–196 (1960); Morton, In Vitro 6:89 (1970); Rutzky and Pumper, In Vitro 9:468 (1974).

Ham's F-12/Dulbecco's Modified Eagle's Medium (e.g., Sigma D6905, D 8900, D 2906, D 9785, D6421)

| SIGMA Prod. # COMPONENT | D6905, D8900 g/L | D 2906 g/L | D 9785 g/L | D 6421 g/L |
|---|---|---|---|---|
| INORGANIC SALTS | | | | |
| $CaCl_2.2H_2O$ | 0.1545 | 0.1545 | — | 0.1545 |
| $CuSO4.5H_2O$ | 0.0000013 | 0.0000013 | 0.0000013 | 0.0000013 |
| $Fe(NO3)3.9H_2O$ | 0.00005 | 0.00005 | 0.00005 | 0.00005 |
| $FeSO_4.7H_2O$ | 0.000417 | 0.000417 | 0.000417 | 0.000417 |
| $MgCl.6H_2O$ | 0.06120 | 0.0612 | — | 0.0612 |
| $MgSO_4$ | 0.04884 | 0.04884 | — | 0.04884 |
| KCl | 0.3118 | 0.3118 | 0.3118 | 0.3118 |
| $NaHCO_3$ | — | — | — | 1.2 |
| NaCl | 6.996 | 6.996 | 6.996 | 6.996 |
| Na2HPO4 | 0.07102 | 0.07102 | 0.07102 | 0.07102 |
| NaH2PO4 | 0.0543 | 0.0543 | 0.0543 | 0.0543 |
| ZnSO4.7H2O | 0.000432 | 0.000432 | 0.000432 | 0.000432 |
| AMINO ACIDS | | | | |
| L-Alanine | 0.00445 | 0.00445 | 0.00445 | 0.0045 |
| L-Arginine.HCl | 0.1475 | 0.1475 | 0.1475 | 0.1475 |
| L-Asparagine.H2O | 0.0075 | 0.0075 | 0.0075 | 0.0075 |
| L-Aspartic Acid | 0.00665 | 0.00665 | 0.00665 | 0.00665 |
| L-Cystine.HCl.H2O | 0.01756 | 0.01756 | 0.01756 | 0.01756 |
| L-Cysteine.2HCl | 0.03129 | 0.03129 | 0.03129 | 0.03129 |
| L-Glutamic Acid | 0.00735 | 0.00735 | 0.00735 | 0.00735 |
| L-Glutamine | 0.365 | 0.365 | — | — |
| Glycine | 0.01875 | 0.01875 | 0.01875 | 0.01875 |
| L-Histidine.HCl.H2O | 0.03148 | 0.03148 | 0.03148 | 0.03148 |
| L-Isoleucine | 0.05447 | 0.05447 | 0.05447 | 0.5447 |
| L-Leucine | 0.05905 | 0.05905 | — | 0.05905 |
| L-Lysine.HCl | 0.09125 | 0.09125 | — | 0.09125 |
| L-Methionine | 0.01724 | 0.01724 | — | 0.01724 |
| L-Phenylalanine | 0.03548 | 0.03548 | 0.03548 | 0.03548 |
| L-Proline | 0.01725 | 0.01725 | 0.01725 | 0.01725 |
| L-Serine | 0.02625 | 0.02625 | 0.02625 | 0.02625 |
| L-Threonine | 0.05345 | 0.05345 | 0.05345 | 0.05345 |
| L-Tryptophan | 0.00902 | 0.00902 | 0.00902 | 0.00902 |
| L-Tyrosine.2Na.2H$_2$O | 0.05579 | 0.05579 | 0.05579 | 0.05579 |
| L-Valine | 0.05285 | 0.05285 | 0.05285 | 0.05285 |
| VITAMINS | | | | |
| D-Biotin | 0.0000035 | 0.0000035 | 0.0000035 | 0.0000035 |
| Choline Chloride | 0.00898 | 0.00898 | 0.00898 | 0.00898 |
| Folic Acid | 0.00265 | 0.00266 | 0.00266 | 0.00266 |
| myo-Inositol | 0.0126 | 0.0126 | 0.0126 | 0.0126 |
| Niacinamide | 0.00202 | 0.00202 | 0.00202 | 0.00202 |
| D-Pantothenic Acid.½Ca | 0.00224 | 0.00224 | 0.00224 | 0.00224 |
| Pyridoxal.HCl | 0.002 | 0.002 | 0.002 | — |
| Pyridoxine.HCl | 0.000031 | 0.000031 | 0.000031 | 0.002031 |
| Riboflavin | 0.000219 | 0.000219 | 0.000219 | 0.000219 |
| Thiamine.HCl | 0.00217 | 0.00217 | 0.00217 | 0.00217 |
| Vitamin B-12 | 0.00068 | 0.00068 | 0.00068 | 0.00068 |

See, e.g., Barnes and Sato, Analyt. Biochem. 102:255–270 (1980).

Citations

All publications or patents cited herein are entirely incorporated herein by reference as they show the state of the art at the time of the present invention and/or to provide description and enablement of the present invention. Publications refer to scientific or patent publications, or any other information available in any media format, including all recorded, electronic or printed formats. The following references are entirely incorporated herein by reference: Ausubel, et al., ed., Current Protocols in Molecular Biology, John Wiley & Sons, Inc., NY, N.Y. (1987–1999); Sambrook, et al., Molecular Cloning: A Laboratory Manual, 2$^{nd}$ Edition, Cold Spring Harbor, N.Y. (1989); Harlow and Lane, Antibodies, a Laboratory Manual, Cold Spring Harbor, N.Y. (1989); Colligan, et al., eds., Current Protocols in Immunology, John Wiley & Sons, Inc., NY (1994–1998); Colligan et al., Current Protocols in Protein Science, John Wiley & Sons, NY, N.Y., (1997–1999).

EXAMPLE 1

Production of Antibodies Enhanced Using Cells Expressing the Human bcl2 Encoding Nucleic Acid Abstract High IgG expressing myeloma cell lines were transfected with the human Bcl2 gene. Stable cell lines were selected and established based on both high IgG production and human Bcl2 expression. In optimal medium, all established Bcl2 cell lines maintained higher viability for a longer period of time than parental control did; however, their cell densities were always low compared to their parents. As cultures aged, Bcl2 cells arrested their growth but maintained a high viability. Parental cultures, on the other hand, kept accumulating cell mass, but the viability dropped sharply. Examining metabolic profiles for glutamine and glucose consumption, and the accumulation of ammonium and lactate showed no obvious differences between these cell lines.

Most Bcl2 cell lines showed higher IgG titers than parental control due to the better growth robustness. In one particular case, the Bcl2 line produced almost twice as much IgG as its parental line.

Non-defined animal derived raw materials, such as primatone and albumin, are common serum replacements in serum free media to support a robust growth of animal cells. The requirement of these compounds decreased in Bcl2 cultures. However, several passages of adaptation were usually required before robust cell growth was observed.

Overall, our data show that over expression of Bcl2 protein improved growth robustness and IgG production of myeloma cells. These advantages are ideal for the improvements of batch or fed-batch type culture systems. However, the concerns that Bcl2 cells are not able to reach high cell density as needed may pose a challenge for its practical applications.

Introduction:

Several successes in the use of monoclonal antibodies (mAb) as therapeutics in recent years have raised great interest in the production of mAbs in large quantity. It has been demonstrated that murine myeloma cells are capable of a high level of IgG expression.

To quickly reach high cell density and to maintain high viability for a prolonged period of time are key factors for the success of manufacturing recombinant proteins. These requirements are true for both perfusion type continuous bioreactors and deep stir tank, fed batch type manufacturing bioprocesses. Therefore, high expressing cell lines with robust growth that can extend the length of their protein production period are the most desirable ones for manufacturing purposes.

Even though murine myeloma cells are well known for their strong growth vigor, many reports indicate that myeloma cells are highly sensitive to apoptosis (programmed cell death) caused by stressed environments or certain chemicals. It has been noted that apoptosis accounts for more than 80% of the cell death observed in myeloma cell cultures. The improvement of growth robustness of myeloma cells by the prevention of apoptosis has been pursued and reported.

The anti-apoptotic function of Bcl2, a membrane protein mainly anchored on the mitochondrial membrane of mammalian cells, has been well documented. Potential mechanisms of these anti-apoptotic activities have been reported. These include formation of heterodimers with pro-apoptotic proteins such as BAX, and also maintenance of an ADP gradient across the mitochondrial membrane.

Applications of Bcl2 in the biopharmaceutical and tissue culture areas have been reported. Several studies have shown that when Bcl2 clones of murine myeloma cells are used as fusion partners, the frequency of hybridoma production is significantly improved. Other studies have reported that Bcl2 clones grow more robustly and produce higher IgG titer than non-Bcl2 clones. Bcl2 transfected hybridoma or myeloma cells also show better resistance to hypoxia or serum depleted conditions, as compared to non-Bcl2 clones.

Use of the Bcl2 gene for the improvement of cell culture quality and recombinant protein production is of great interest to Centocor. Here we report that growth robustness and IgG production of several Bcl2 cultures derived from high IgG producing myeloma cell lines were improved.

Materials and Methods:

Vectors, Transformation and Plasmid DNA Preparation:

The human Bcl2 gene was obtained from ATCC (pB4, ATCC cat. #79804). Restriction enzymes were obtained from New England Biolabs. Plasmid pZeoSV2, Zeocin and Low Salt broth were purchased from Invitrogen.

Transformation was performed by electroporation (Cell Porator—*E. coli* pulser from *Life Science Technology*). Competent DH-10B cells were purchased from GibcoBRL (cat. #18297-010). Zeocin was purchased from *Invitrogen* (cat. #46-0509) and was added to low salt LB broth or agar (Invitrogen cat. #0100-04) to a final concentration of 50 ug/ml. Electroporated bacterial cells were recovered in SOC (GibcoBRL cat. #15544-034) for one hour before being subjected to Zeocin selection. Plasmid DNA was prepared using the Promega Wizard plus SV (cat. #A1460, for miniprep) or Wizard plus (cat. #A7640, for midiprep) kits. All digested DNA was characterized using 0.8% agarose (Sigma cat. #A6103) prepared and run in 1X TAE buffer (GibcoBRL cat. #24710-030). DNA sequencing was carried out in a Perkin-Elmer ABI Prism 377 (done by Wistar Institute, Pa., USA).

Transfections and Tissue Culture:

Several IgG producing cell lines developed by Centocor were transfected with the pZeoSV2Bcl2 plasmid. Overnight cultures were washed and resuspended in 1X PBS at $1 \times 10^7$ cells/well. Electroporator (Cell Porator, Life Science Technology) was set at 1180 capacitance/200 volts. After shocking and overnight recovery in growth medium, cells were harvested and resuspended in growth medium with Zeocin at 100 ug/ml. Cells were then seeded in 96-well plates with cell density at $1 \times 10^4$ cells/well. Zeocin resistant colonies usually appeared in about two weeks at 20% to 30% occupancy (2 to $3 \times 10^{-5}$ transfection efficiency). These colonies were expanded and subjected to a second round of screening for high IgG expression.

Detection of Chimeric IgG:

Chimeric IgG was quantified by nephelometry using the Beckman Array Protein System. For reactions, 300 ul of culture supernatants were mixed with rabbit anti-human IgG (H+L) (Jackson Immuno Research Code #309-001-0039) to form immunoprecipitates for detection. A standard curve was generated from chimeric IgG of anti-CD-4 prepared by Centocor.

Bcl2 Western:

1 to 2×10^6 cells were washed with 1X PBS one time. Cells were spun down at 2000 rpm for 10 minutes in a microfuge. Cell pellets were resuspended in 40 ul of lysis buffer. This lysis buffer was prepared with 1% TritonX in TSA buffer (10 mM Tris, 140 mM NaCl). Lysates were spun for 5 minutes at 10000 rpm to remove any insoluble particles.

10% gradient polyacrylamide gels were obtained from BIO RAD. Nitrocellulose was purchased from Schleicher & Schuell. Electrophoresis was performed at 25 mA. Electroblotting was performed at 100 mA. Monoclonal antibody specific to human Bcl2 was purchased from Santa Cruz Biotechnology, Inc. (Cat. # sc-509)

Bioprofile Analysis:

Metabolic profiles were obtained using Bioprofile 200 from NOVA Biomedical.

Results and Discussion:

Construction of Bcl2 Expression Vectors and Mammalian Cell Transfection:

A 0.9 kb human Bcl2 gene was excised from pB4 (ATCC 79804) by EcoR1 digestion and cloned into the EcoR1 site of the pZeoSV2(+) plasmid. Selection was performed at a Zeocin concentration of 50 ug/ml in low salt agar or broth. Orientation of insert was determined by several restriction enzyme digestions and then confirmed by DNA sequencing (Perkin-Elmer ABI Prism 377). The new plasmid was called pZeoSV2Bcl2. A map of pZeoSV2Bcl2 are shown in FIG. 1.

Bcl2 Cell Line and Bcl2 Expression:

Sp2/0 and Sp2/0 derived IgG producing cell lines were electroporated with pZeoSV2Bcl2 DNA and then selected with Zeocin (100 ug/ml). Two weeks after antibiotic selection, Zeocin resistant colonies were observed in 96 well plates. Transfection efficiency was about 2 to 3×10^-5. Colonies were expanded and screened for IgG titer in T-25 flasks. Only clones with high IgG expression were expanded for further development. Three Bcl2 clones were used in this study. One is derived from SP2/0, the other two are the derivatives of two IgG producing cell lines, IgG R and IgG M.

Figure 2:
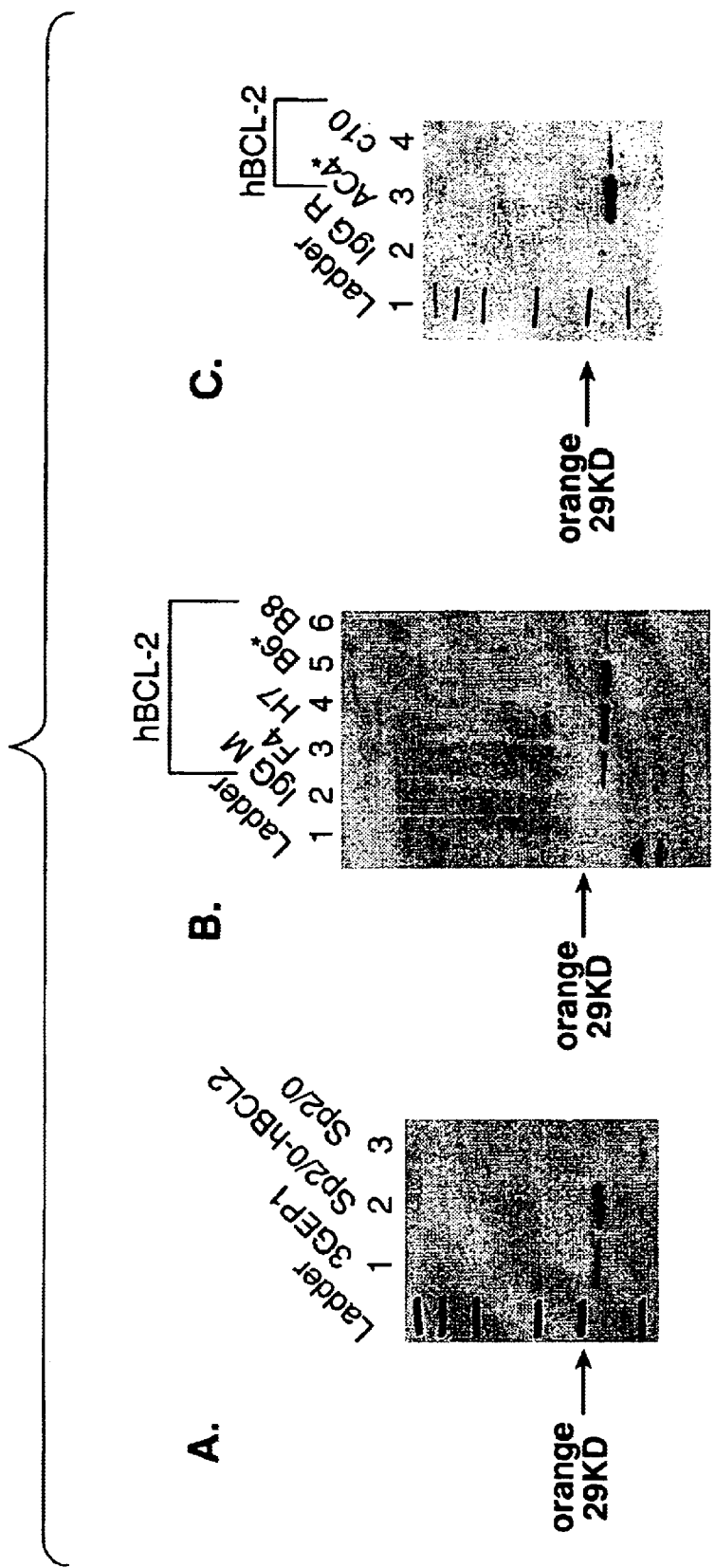
FIGS. 2A–C are representations of Western blots showing expression of human Bcl2 protein in Bcl2 clones of various myeloma cell lines. $10^6$ cells were lysed in 150 ul lysis buffer. 20 ul of lysate from each sample was loaded to 10% polyacryamine gel. Monoclonal antibody specific to human Bcl2 was purchased from Santa Cruz Biotechnology, INC. (sc-509). A 29 KD band were shown in all Bcl2 clones, but not in all parental lines. (2A) Samples from Sp2/0(lane 4) and two Bcl2/Sp2/0 clones (lane 2 and 3). (2B) Samples from IgG M (lane 2) and Ig M/Bcl2 clones (lane 3, 4, 5 and 6). (2C) Samples from IgG R (lane 2) and IgG R/Bcl2 clones (lane 3 and 4).
Figure 3B:
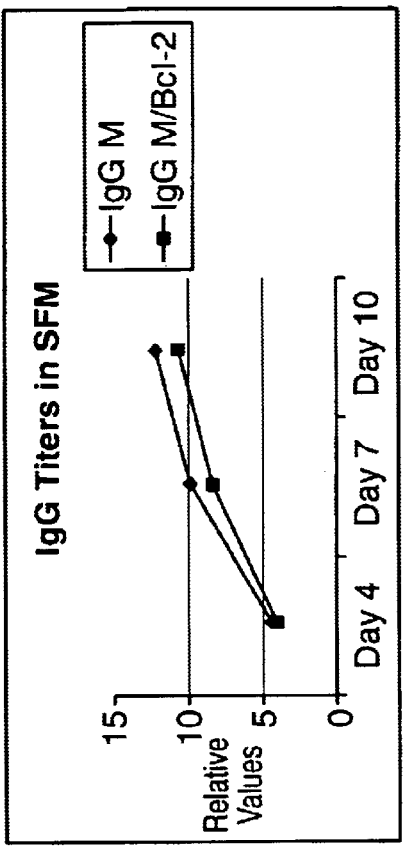
FIGS. 3A–D are graphical representations showing ten day growth profile in SFM complete medium for the IgG M and IgG M/Bcl-2 cell lines. T25 flasks were inoculated at $0.1 \times 10^6$ cells/ml. (3A) Viability on day 4, 7 and 10; (3B) IgG production on day 4, 7 and 10; (3C) total cell density; (3D) viable cell density.
Figure 3D:
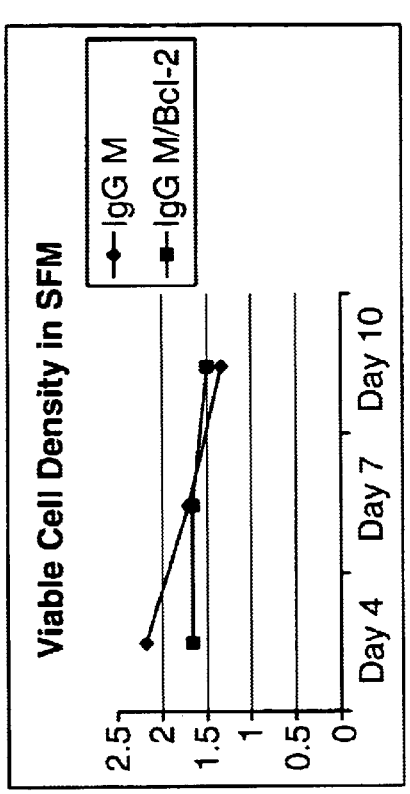
Figure 3A:
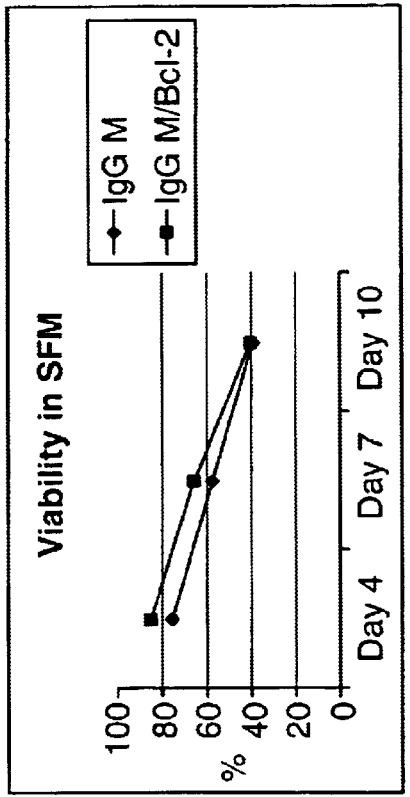
Figure 3C:
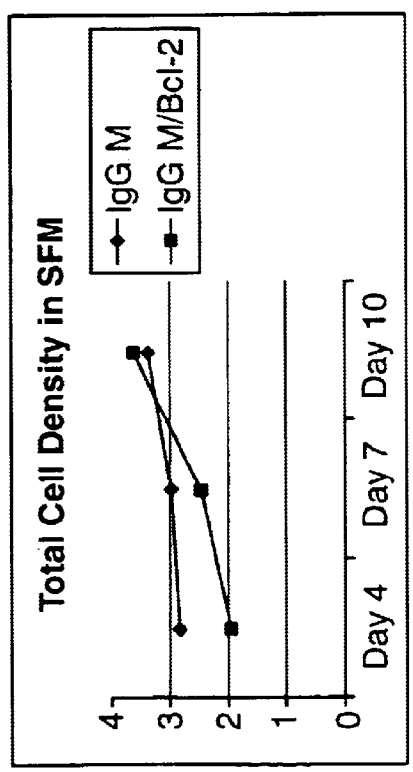

The 29 KD human Bcl2 protein was found in all listed Bcl2 clones by western blot (FIG. 2).

Growth Profile and IgG Production of Bcl2 Lines in an Animal Protein Supplemented Serum Free Medium:

In a serum free, animal protein containing medium (SFM), the Bcl2 cultures of IgG R (IgG R/Bcl2), IgG M (IgG M/Bcl2) and Sp2/0 (Sp2/0 Bcl2) lasted longer than their parental cells. Among them, IgG R/Bcl2 and Sp2/0Bcl2 lasted twice as long as their parental cultures based on the days that viability stayed above 40% (14 days vs 7 days). All Bcl2 clones failed to reach the same cell density that their parents could reach. Among them, IgG R/Bcl2 reached only half of the density that its parent reached (FIGS. 3, 4 and 5).

Both IgG R/Bcl2 and IgG M/Bcl2 were selected for high IgG expression as well as satisfactory expression of the 29 KD human Bcl2 gene product. The IgG titer of the IgG M/Bcl2 clones was close to that of the parental cell line. The specific productivity (IgG per cell basis) was about the same or slightly higher than parents due to the lower cell density observed in the IgG M/Bcl2 cell cultures (FIG. 3).

Figure 4:
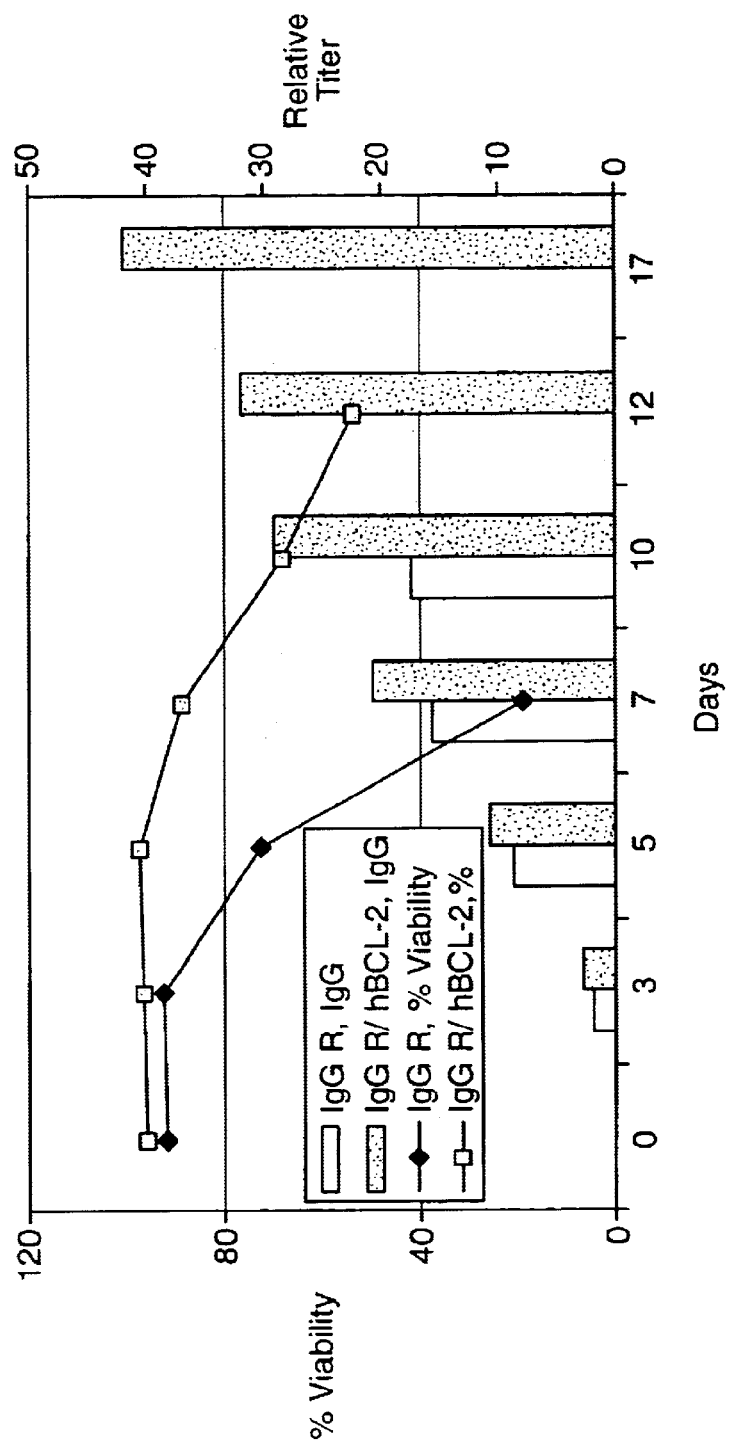
FIG. 4: is a graphical representation of seventeen day growth profile of IgG R and IgG R/hBCL-2 cell lines in SFM complete medium. Spinner flasks were inoculated at 0.1×10^6 cells/mL. The hBCL-2 line can survive 10 days longer than it's parental line in optimal medium and produce twice as much total titer. Total density reached 5×10^6 cells/mL for IgG R and 2.5×10^6 cells/mL for the hBCL-2 line. Both cell lines grew to a viable density of 2–2.5×10^6 cells/mL.
Figure 5A:
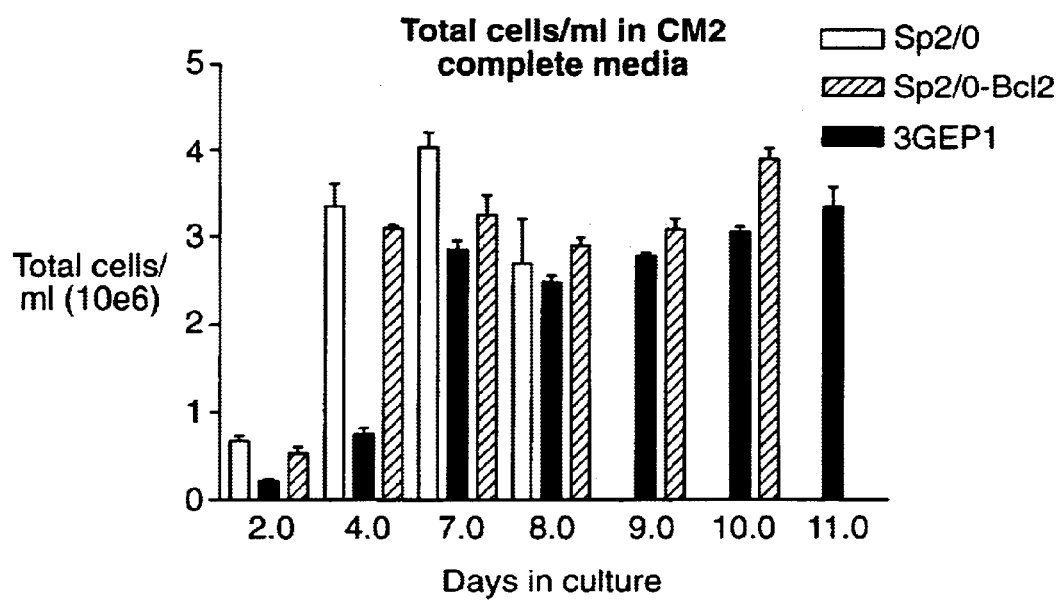
FIGS. 5A–D are graphical representations showing Sp2/0-BCL2 and 3GEP1 Growth Profiles in CM2 complete media. Duplicate 75 cm2 T-flasks were seeded at 0.1×10$^6$ cells/ml in 20 ml of CM2 Complete media. Total cell density (5A), viable cell density (5B), % viability (5C), and cell doubling times (5D), were determined on the days indicated.
Figure 5B:
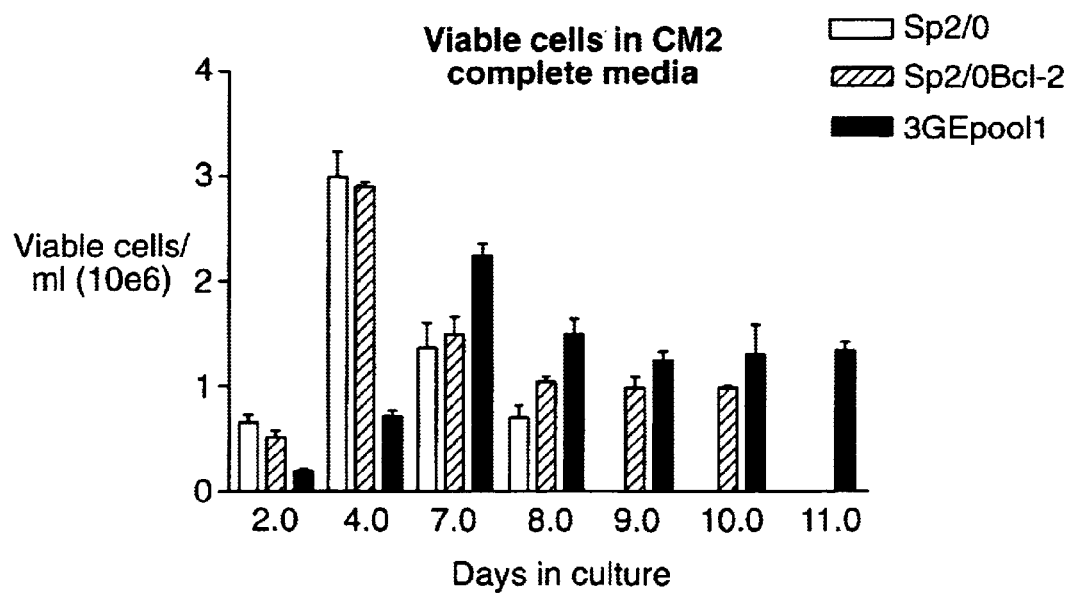
Figure 5C:
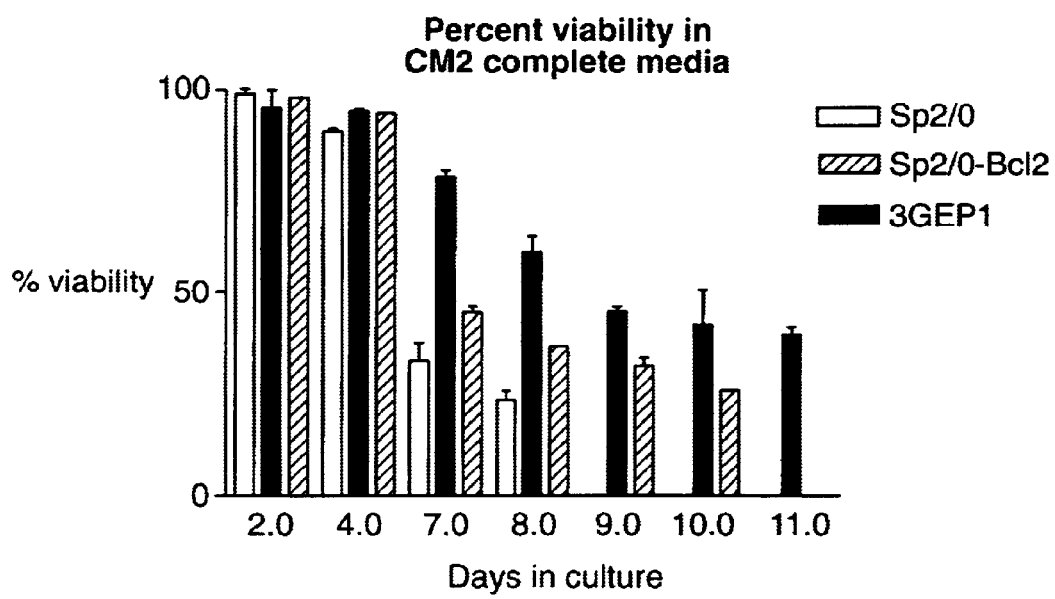
Figure 5D:
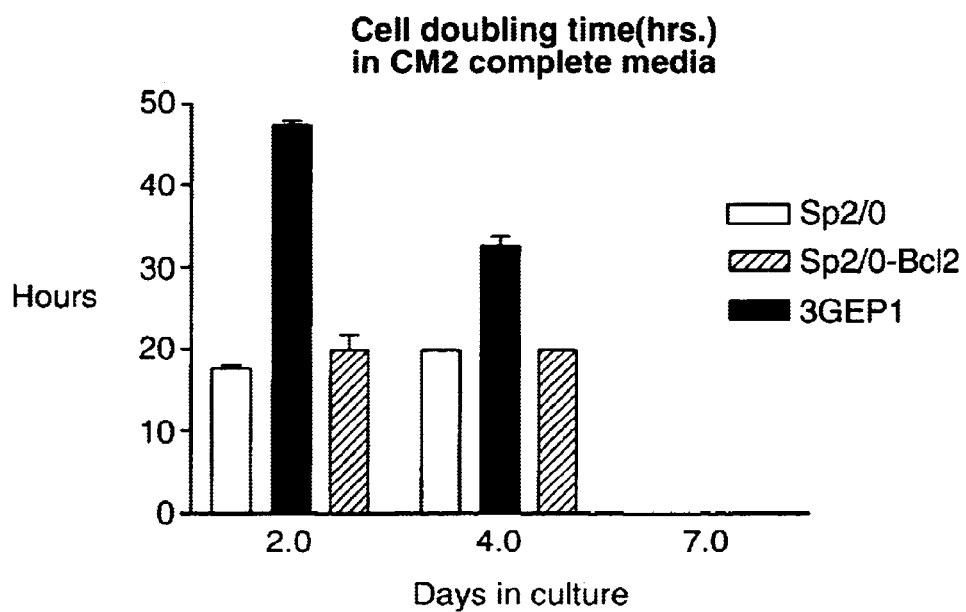
Figure 6:
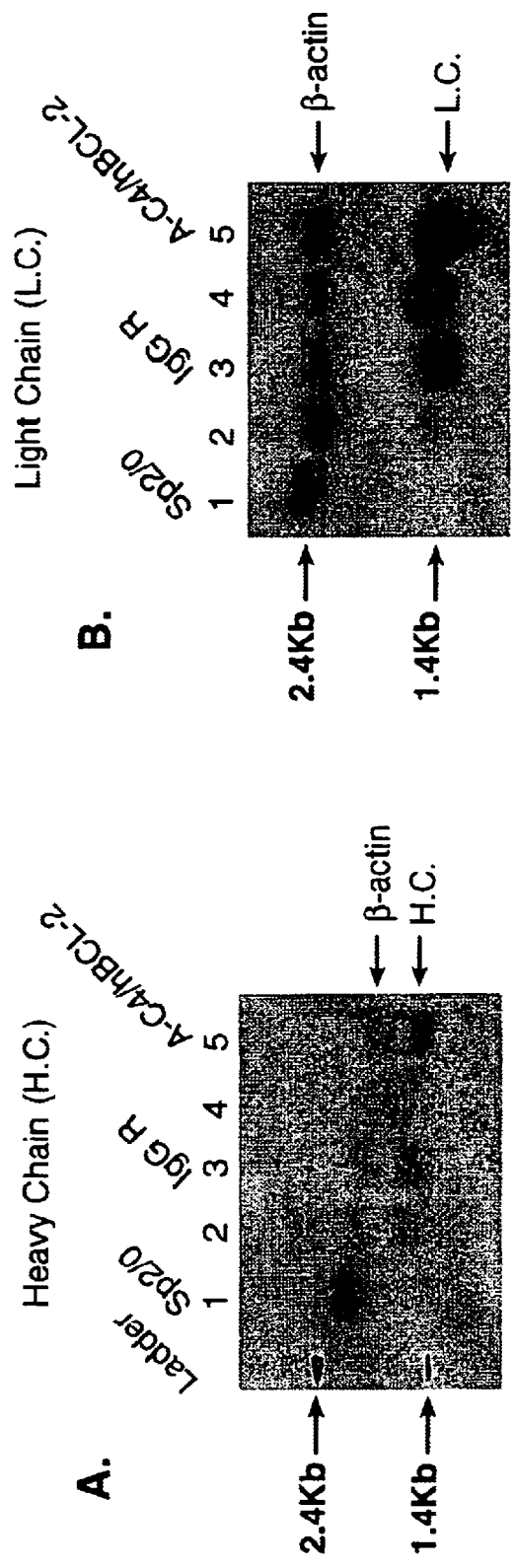
FIGS. 6A–B: are representation of Northern blots showing expression of heavy chain and light chain genes in myeloma cell lines, Sp2/0, IgG R and IgG R/Bcl2. Northern blots contain 18 ug total RNA for each sample. Total RNA from each indicated cell lines were probed with constant regions of heavy chain (3.1 kb HindIII-SSp1 fragment) light chain (4.9 kb HindIII-BglII fragment) and beta-actin gene (1.3 kb EcoRI-NotI fragment). (A) heavy chain expression. See lane 3 for IgG R and lane 5 for IgG R/Bcl2 (B) light chain expression. See lane 3 for IgG R and lane 5 for IgG R/Bcl2.

Surprisingly, the IgG titer of IgG R/Bcl2 was twice as much as the titer that its parental cells produced, and even higher for specific productivity since its cell density was lower than that of its parental cell culture (FIG. 4). When the level of transcription was examined by northern blot analysis, both heavy and light chain transcription were found to be almost twice as high as those of the observed parental cell lines (FIG. 6). Apparently, increased transcription accounts for the increase in IgG production of the IgG R/Bcl2 clone.

Growth profile and IgG production of Bcl2 lines in animal protein limited serum free medium: Animal protein based raw materials, such as albumin and primatone, are common additives in serum free medium to support the robust growth of animal cells.

Figure 7A:
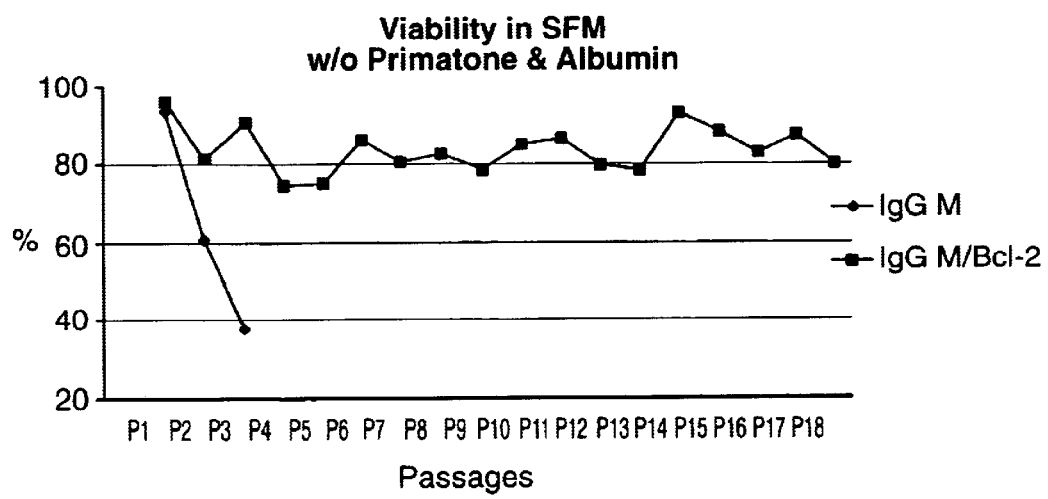
FIGS. 7A–B are graphical representations of continuous cultures for 18 passages in primatone and albumin depleted SFM for the IgG M/Bcl-2 cell line. The IgG M cell line crashed at passage 3 in the same medium. T150 flasks were inoculated at 0.2×10^6 cells/ml. After passage 13, the IgG M/Bcl-2 cell line was expanded to spinner flasks. (7A) Viability; (7B) Total cell density.
Figure 7B:
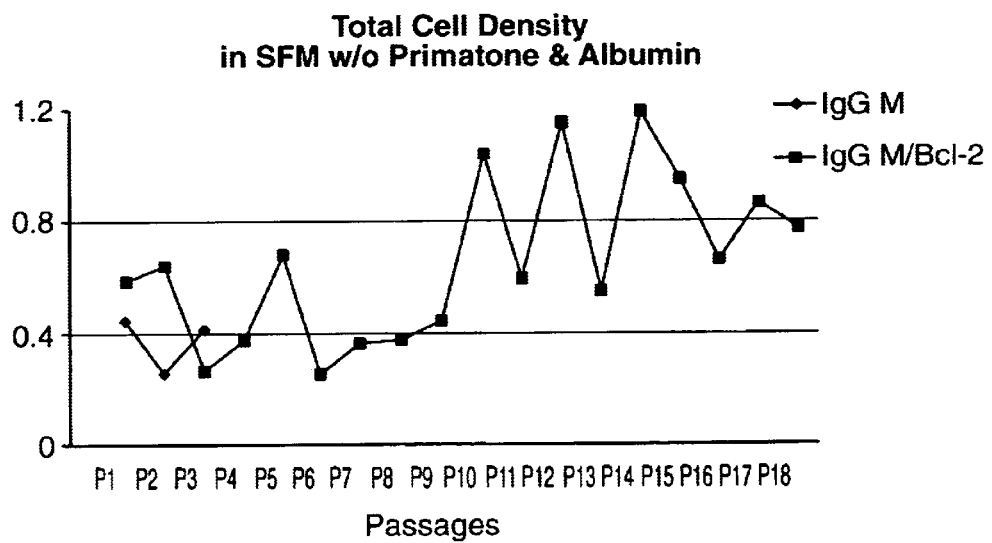

FIG. 7 shows a comparison of the IgG M producing cell line to its Bcl2 clone in SFM medium lacking primatone and albumin. Viability of the parental cells declined sharply; these cells could not be cultured beyond two or three passages. In contrast, the Bcl2 line was able to survive and then regain growth with a doubling time of approximately 35 to 40 hours and viability above 80% for more than 20 passages. Similar responses were also observed in several other Bcl2 clones of IgG M except that a shorter time period was used. The IgG production of Bcl2 clones was severly reduced under primatone/albumin depleted serum free conditions; it was approximately 50% of the titer that these Bcl2 cells could produce in complete SFM medium. This severe reduction was caused mainly by the low cell density of Bcl2 cultures in primatone and albumin depleted medium; a less adverse effect was observed when specific productivity was used as the basis for comparison (FIG. 8).

Figure 9:
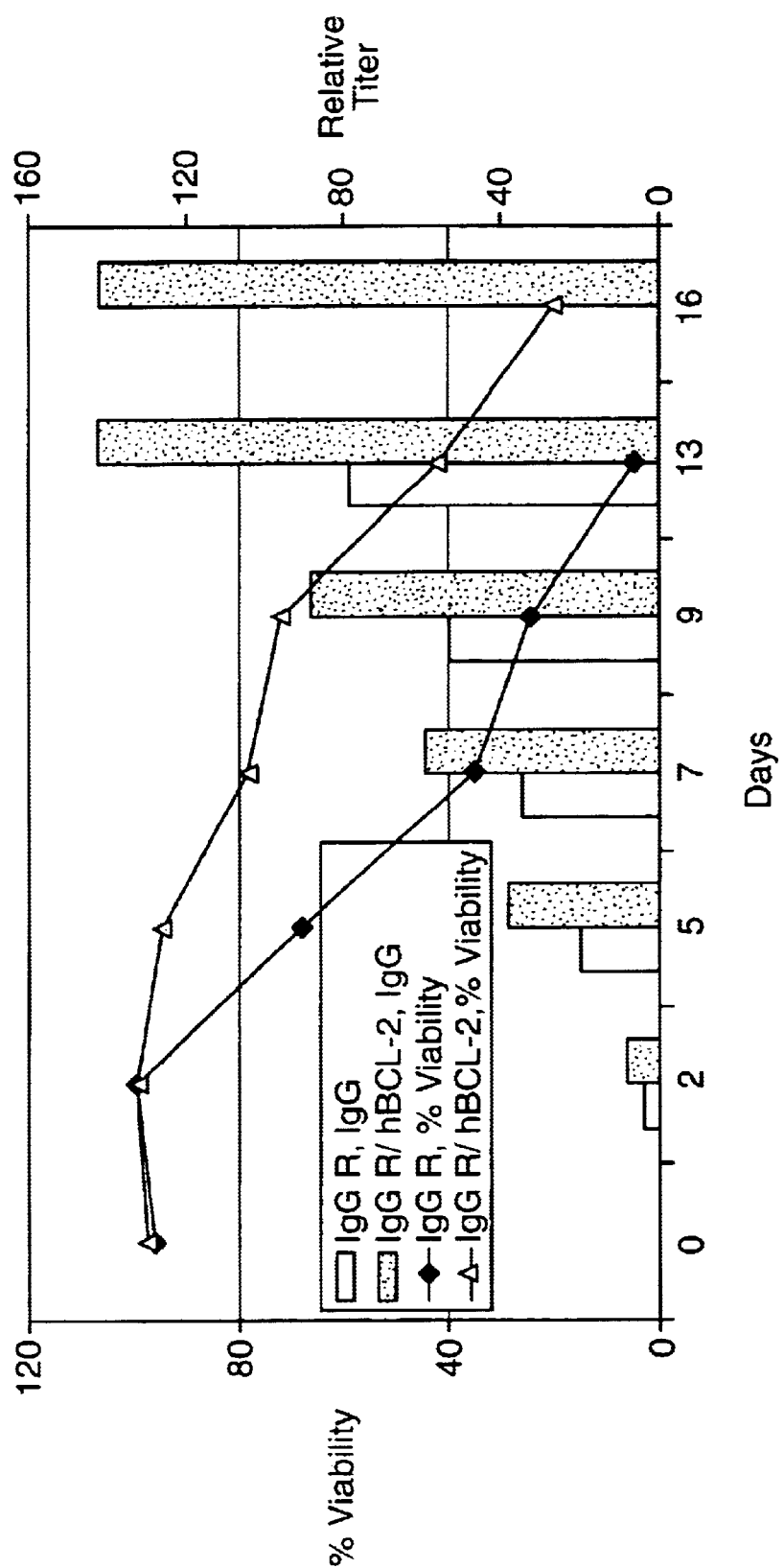
FIG. 9 is a graphical representation showing sixteen day growth profile of IgG R and IgG/hBCL-2 cell lines in primatone and albumin free SFM medium. Spinner flasks were seeded at 0.2×10^6 cells/mL. The hBCL-2 line can maintain higher viability longer and produce almost double the protein than it's parental line. Total density reached 3×10^6 cells/mL for IgG R and 2×10^6 cells/mL for the hBCL-2 line. Both cell lines reached viable density of 2×10^6 cells/mL.
Figure 11A:
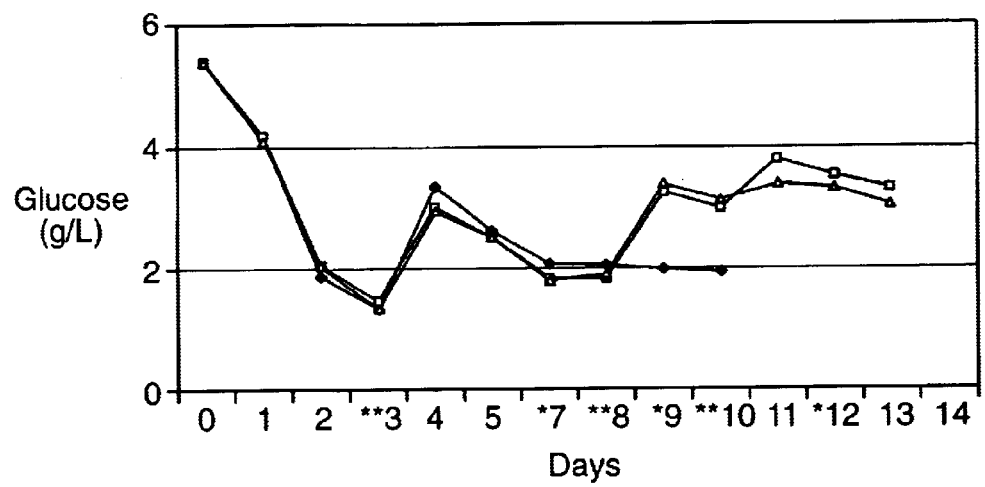
FIGS. 11A–D are graphical representations showing Metabolic Profiles of IgG R and IgG R/hBCL-2 cell lines from Fed-Batch experiment in spinners. Samples were assayed before feeding the cultures with glutamine and/or glucose. *=fed w/glutamine only. =fed w/glutamine and glucose. (11A) Glucose; (11B) Glutamine; (11C) Lactate; (11D**) Ammonium.
Figure 11B:
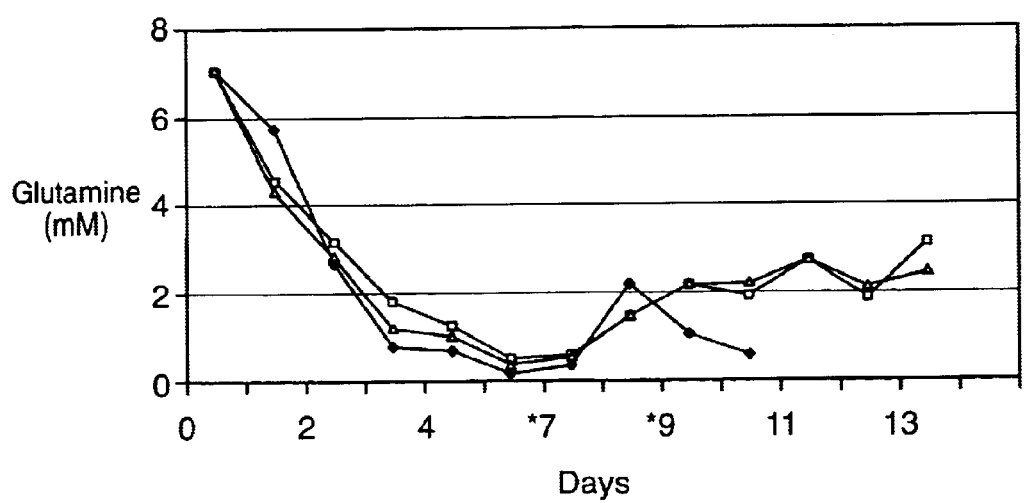
Figure 11C:
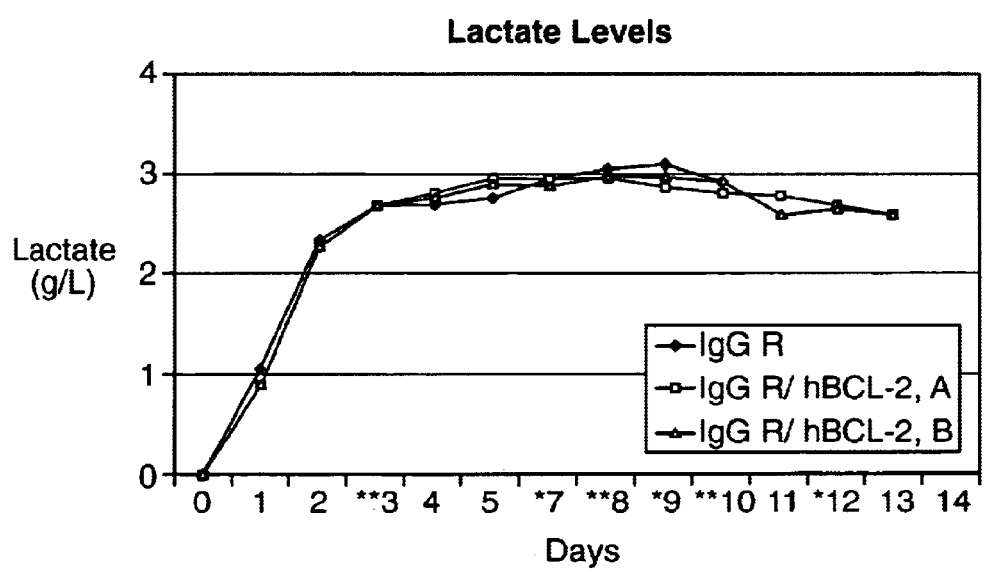
Figure 11D:
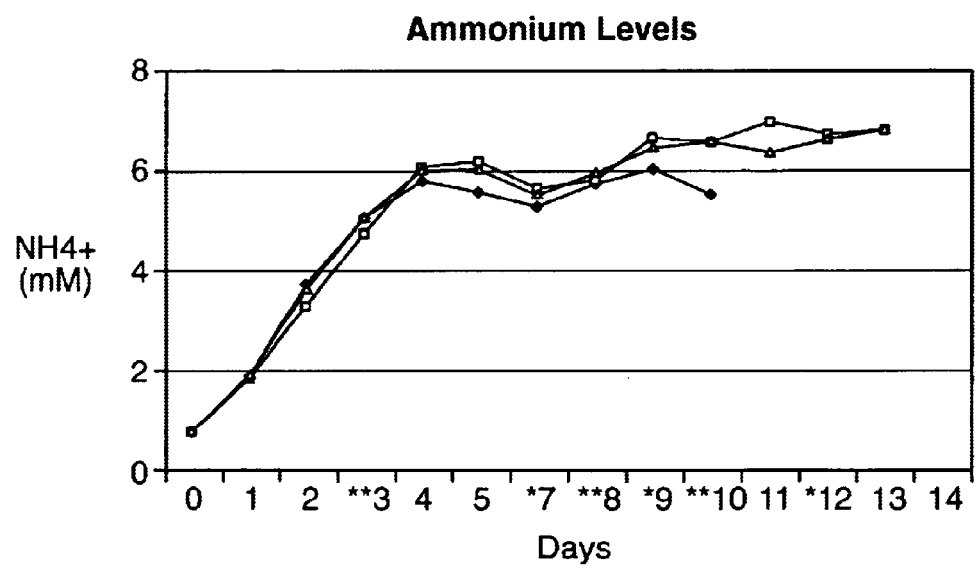

Resistance to primatone and albumin withdrawal was also observed in Bcl2 clones of the IgG R producing cell line. In this case, the parental line grew to a total cell density of 3×10^6 cells/ml with a sharp drop in viability after day 2. Viability reached only 40% on day 7. In contrast, although the cell density of the Bcl2 clone of IgG R reached only 1.7×10^6 cells/ml on day 7, the viability was still about 80% at that time. The viability of this Bcl2 clone remained above 40% on day 13, which was almost twice as long as its parental cells could survive. The IgG titer of this clone was not severely affected in primatone and albumin stressed conditions, as was observed in the Bcl2 clone of IgG R. FIG. 9 shows that in primatone and albumin stressed conditions, the IgG titer of Bcl2 clone of IgG R was about two folds higher than that of its parental culture. Specific productivity on a per cell basis was even more than two folds higher since the cell density of the Bcl2 culture was less than that of its parental culture. A similar response to primatone and albumin withdraw was also observed in some other Bcl2 clones of IgG R, except that the IgG production of these Bcl2 clones was only slightly higher than that of the parental cells.

Responses of Bcl2 Cultures to Glucose and Glutamine Feed in Animal Protein Supplemented Serum Free Medium:

Bcl2 cells could not reach the same cell density that their parental cells did in batch culture. To rule out nutrient depletion as the cause of low cell density growth, L-glutamine or glucose was added to the cultures when stationary phase was reached.

The IgG R producing cell line and its Bcl2 clone were chosen for this experiment because of their adequate growth robustness and IgG production. In this experiment, L-glutamine and/or glucose was added to the cultures in complete SFM medium on day 3. NOVA analysis was performed on and after day 3 to monitor the metabolic profile of the cultures.

Both parental and Bcl2 cultures quickly reached stationary phase about 3 days after the cultures were started. At this point, the total cell density of the parental culture was slightly higher than that of the Bcl2 culture (3.5×10^6 cells/ml vs 3×10^6 cells/ml), but the viability was significantly lower (78% for the parental culture and 95% for the Bcl2 clone). Overall, the viable cell density of the parental and Bcl2 cultures was about the same before feeding was started.

L-glutamine and/or glucose feed did not increase viable cell density in either the Bcl2 or the parental cell cultures. The total cell density of the parental culture went up to 7×10^6 cells/ml on day 6, with viability at only 30%. On the other hand, total cell density of the Bcl2 culture barely increased after feeding but the viability remained at 60% up to day 8, and was still above 40% even at day 11. The IgG titer of the Bcl2 culture had been higher than that of its parental culture during the entire course of cell growth. It was not measured to be twice as high as the IgG titer observed in batch culture, though. When cell number was taken into consideration, the specific production (IgG per cell basis) of Bcl2 cells was expected to be more than double that of the parental cells (FIG. 10).

The consumption of L-glutamine and glucose by animal cells results in an accumulation of ammonium and lactate, respectively. Myeloma cells have been shown to be very sensitive to ammonium or lactate accumulation. Our data show that a steep drop in viability occurred in the parental cells when ammonium concentrations rose from 3 to 5 mM. At the same time, the concentrations of lactate only increased from 2.5 to 2.8 ug/ml. The accumulation of ammonium and lactate in Bcl2 cultures was almost identical to that of the parental cells, but the viability of the Bcl2 cultures remained high (60% vs 80%) even when ammonium concentrations increased to 6 or 7 mM. As reported elsewhere, we have also observed that Bcl2 cultures are much more capable of surviving in toxic environments than are their parental cells (FIG. 11).

Figure 10:
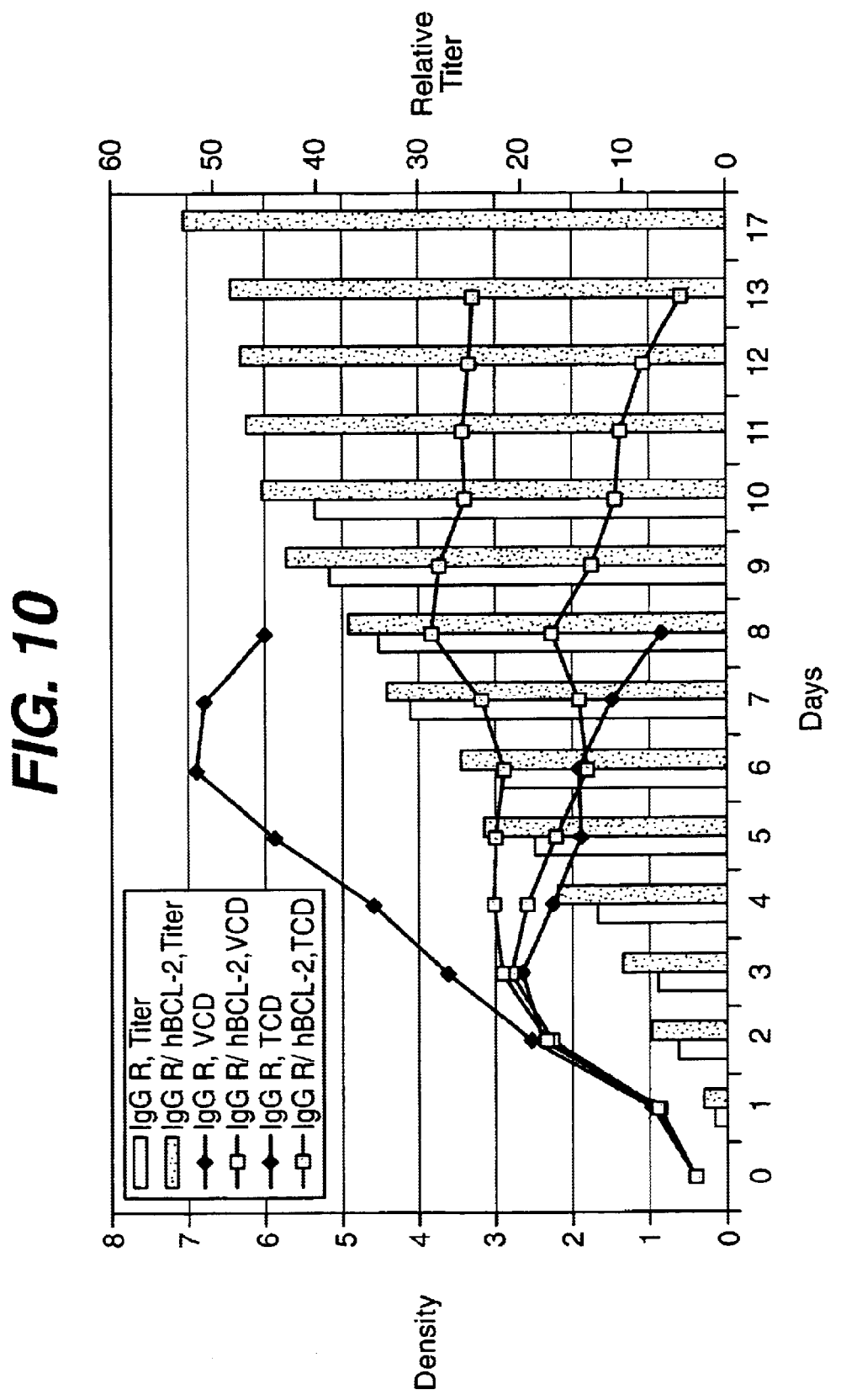

FIG. 10 shows that the total cell density of the Bcl2 culture did not change after day 3, while the parental culture's total cell density kept increasing with fewer and fewer viable cells surviving. Since it is known that resting cells are much more resistant to stressful conditions than active growing cells, it is possible that the reason the Bcl2 cells are capable of surviving under high ammonium conditions may be due to their extended cell growth arrest. This point is yet to be confirmed by cell cycle analysis.

Figure 12:
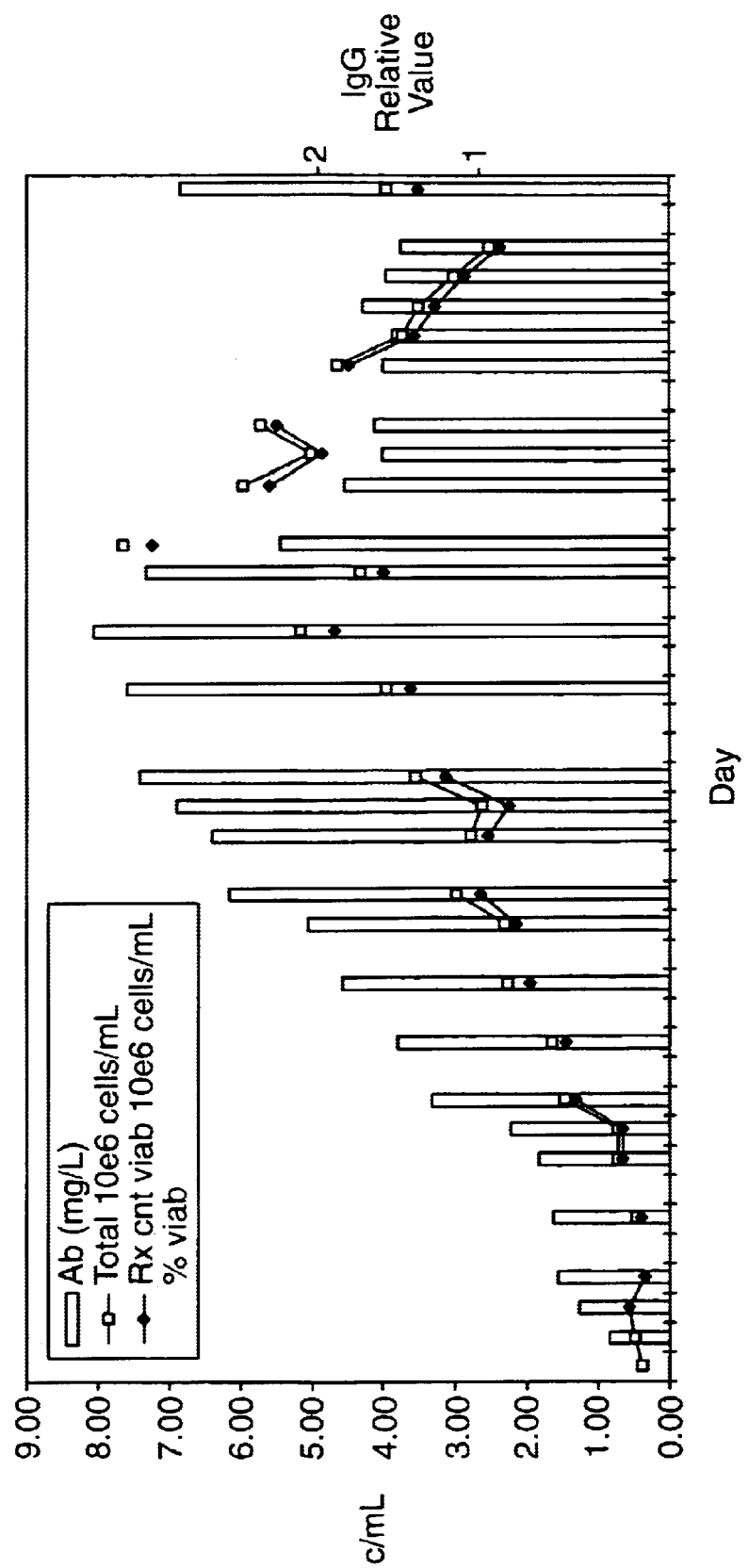
FIG. 12 is a graphical representation showing growth profile and IgG production of clone IgG R/Bcl2 in a perfusion type bioreactor.
Figure 13:
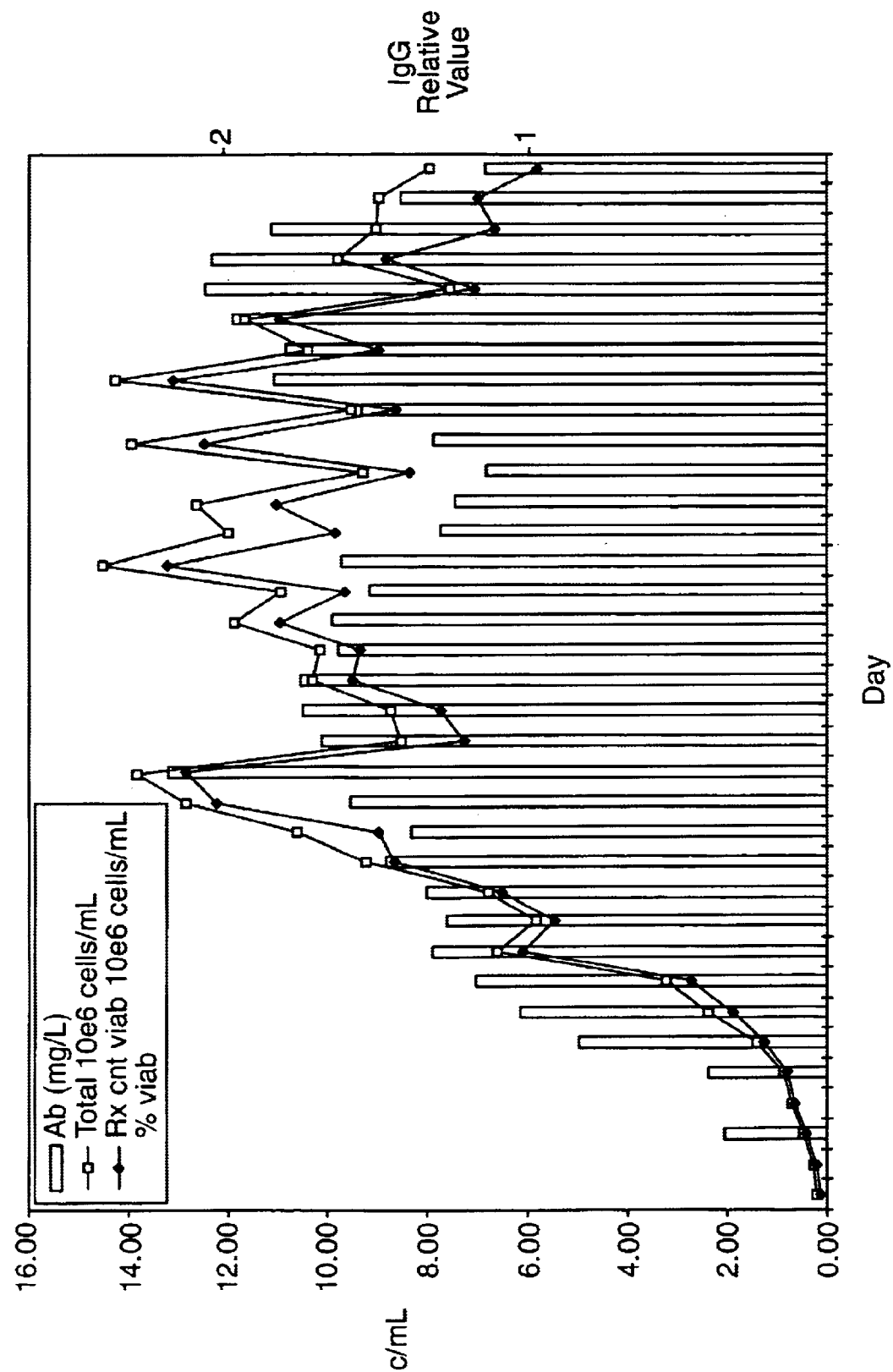
FIG. 13 is a graphical representation showing growth profile and IgG production of clone IgG R in a perfusion type bioreactor

Summary:

1. Bcl2 clones were derived from two IgG producing myeloma cell lines and Sp2/0. All Bcl2 clones expressed the 29 KD human Bcl2 protein.
2. All IgG producing Bcl2 clones maintained a high IgG expression phenotype.
3. Bcl2 cultures survived twice as long as their parental cell cultures in optimal medium, but their cell density was 20 to 50% lower than that of their parental cultures.
4. L-glutamine/glucose feed did not improve the cell density of the Bcl2 cultures.
5. The IgG titer of the Bcl2 cultures was either close to or slightly higher than the titer of their parental cells even though their cell density was generally much lower.
6. Bcl2 cultures survived in serum free, animal protein stressed medium, while their parental cells could not.
7. Bcl2 cultures were capable of resisting much higher ammonium concentrations than their parental cells.
8. The low cell density growth of Bcl2 cultures poses the main concern for their practical application in the biopharmaceutical industry. This concern was supported by data from two bioreactor runs (FIGS. 12 and 13).

SEQUENCE LISTING

<160> NUMBER OF SEQ ID NOS: 14

<210> SEQ ID NO 1
<211> LENGTH: 239
<212> TYPE: PRT
<213> ORGANISM: Homo sapiens

<400> SEQUENCE: 1

```
Met Ala His Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Ala
            20                  25                  30

Gly Asp Val Gly Ala Ala Pro Pro Gly Ala Ala Pro Ala Pro Gly Ile
        35                  40                  45

Phe Ser Ser Gln Pro Gly His Thr Pro His Pro Ala Ala Ser Arg Asp
    50                  55                  60

Pro Val Ala Arg Thr Ser Pro Leu Gln Thr Pro Ala Ala Pro Gly Ala
65                  70                  75                  80

Ala Ala Gly Pro Ala Leu Ser Pro Val Pro Pro Val Val His Leu Ala
                85                  90                  95

Leu Arg Gln Ala Gly Asp Asp Phe Ser Arg Arg Tyr Arg Gly Asp Phe
            100                 105                 110

Ala Glu Met Ser Ser Gln Leu His Leu Thr Pro Phe Thr Ala Arg Gly
        115                 120                 125

Arg Phe Ala Thr Val Val Glu Glu Leu Phe Arg Asp Gly Val Asn Trp
    130                 135                 140
```

```
Gly Arg Ile Val Ala Phe Phe Glu Phe Gly Val Met Cys Val Glu
145                 150                 155                 160

Ser Val Asn Arg Glu Met Ser Pro Leu Val Asp Asn Ile Ala Leu Trp
            165                 170                 175

Met Thr Glu Tyr Leu Asn Arg His Leu His Thr Trp Ile Gln Asp Asn
            180                 185                 190

Gly Gly Trp Asp Ala Phe Val Glu Leu Tyr Gly Pro Ser Met Arg Pro
            195                 200                 205

Leu Phe Asp Phe Ser Trp Leu Ser Leu Lys Thr Leu Leu Ser Leu Ala
            210                 215                 220

Leu Val Gly Ala Cys Ile Thr Leu Gly Ala Tyr Leu Ser His Lys
225                 230                 235

<210> SEQ ID NO 2
<211> LENGTH: 205
<212> TYPE: PRT
<213> ORGANISM: Homo sapiens

<400> SEQUENCE: 2

Met Ala His Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Ala
            20                  25                  30

Gly Asp Val Gly Ala Ala Pro Pro Gly Ala Ala Pro Ala Pro Gly Ile
            35                  40                  45

Phe Ser Ser Gln Pro Gly His Thr Pro His Pro Ala Ala Ser Arg Asp
        50                  55                  60

Pro Val Ala Arg Thr Ser Pro Leu Gln Thr Pro Ala Ala Pro Gly Ala
65                  70                  75                  80

Ala Ala Gly Pro Ala Leu Ser Pro Val Pro Pro Val Val His Leu Ala
                85                  90                  95

Leu Arg Gln Ala Gly Asp Asp Phe Ser Arg Arg Tyr Arg Gly Asp Phe
            100                 105                 110

Ala Glu Met Ser Ser Gln Leu His Leu Thr Pro Phe Thr Ala Arg Gly
            115                 120                 125

Arg Phe Ala Thr Val Val Glu Glu Leu Phe Arg Asp Gly Val Asn Trp
        130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
            165                 170                 175

Met Thr Glu Tyr Leu Asn Arg His Leu His Thr Trp Ile Gln Asp Asn
            180                 185                 190

Gly Gly Trp Val Gly Ala Ser Gly Asp Val Ser Leu Gly
            195                 200                 205

<210> SEQ ID NO 3
<211> LENGTH: 239
<212> TYPE: PRT
<213> ORGANISM: Homo sapiens

<400> SEQUENCE: 3

Met Ala His Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Ala
            20                  25                  30
```

```
Gly Asp Val Gly Ala Ala Pro Pro Gly Ala Ala Pro Ala Pro Gly Ile
            35                  40                  45

Phe Ser Ser Gln Pro Gly His Thr Pro His Pro Ala Ala Ser Arg Asp
            50                  55                  60

Pro Val Ala Arg Thr Ser Pro Leu Gln Thr Pro Ala Ala Pro Gly Ala
65                  70                  75                  80

Ala Ala Gly Pro Ala Leu Ser Pro Val Pro Val Val His Leu Ala
                85                  90                  95

Leu Arg Gln Ala Gly Asp Asp Phe Ser Arg Arg Tyr Arg Gly Asp Phe
            100                 105                 110

Ala Glu Met Ser Ser Gln Leu His Leu Thr Pro Phe Thr Ala Arg Gly
            115                 120                 125

Arg Phe Ala Thr Val Val Glu Glu Leu Phe Arg Asp Gly Val Asn Trp
            130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
            180                 185                 190

Gly Gly Trp Asp Ala Phe Val Glu Leu Tyr Gly Pro Ser Met Arg Pro
            195                 200                 205

Leu Phe Asp Phe Ser Trp Leu Ser Leu Lys Thr Leu Leu Ser Leu Ala
            210                 215                 220

Leu Val Gly Ala Cys Ile Thr Leu Gly Ala Tyr Leu Ser His Lys
225                 230                 235

<210> SEQ ID NO 4
<211> LENGTH: 21
<212> TYPE: PRT
<213> ORGANISM: Homo sapiens

<400> SEQUENCE: 4

Asp Met Phe Ser Asp Gly Asn Phe Asn Trp Val Arg Val Val Ala Leu
1               5                   10                  15

Phe Tyr Phe Ala Ser
            20

<210> SEQ ID NO 5
<211> LENGTH: 175
<212> TYPE: PRT
<213> ORGANISM: Homo sapiens

<400> SEQUENCE: 5

Met Asp Glu Asp Val Leu Pro Gly Glu Val Leu Ala Ile Glu Gly Ile
1               5                   10                  15

Phe Met Ala Cys Gly Leu Asn Glu Pro Glu Tyr Leu Tyr His Pro Leu
            20                  25                  30

Leu Ser Pro Ile Lys Leu Tyr Ile Thr Gly Leu Met Arg Asp Lys Glu
            35                  40                  45

Ser Leu Phe Glu Ala Met Leu Ala Asn Val Arg Phe His Ser Thr Thr
            50                  55                  60

Gly Ile Asn Gln Leu Gly Leu Ser Met Leu Gln Val Ser Gly Asp Gly
65                  70                  75                  80

Asn Met Asn Trp Gly Arg Ala Leu Ala Ile Leu Thr Phe Gly Ser Phe
            85                  90                  95
```

```
Val Ala Gln Lys Leu Ser Asn Glu Pro His Leu Arg Asp Phe Ala Leu
            100                 105                 110

Ala Val Leu Pro Val Tyr Ala Tyr Glu Ala Ile Gly Pro Gln Trp Phe
            115                 120                 125

Arg Ala Arg Gly Gly Trp Arg Gly Leu Lys Ala Tyr Cys Thr Gln Val
            130                 135                 140

Leu Thr Arg Arg Arg Gly Arg Arg Met Thr Ala Leu Leu Gly Ser Ile
145                 150                 155                 160

Ala Leu Leu Ala Thr Ile Leu Ala Ala Val Ala Met Ser Arg Arg
                165                 170                 175

<210> SEQ ID NO 6
<211> LENGTH: 211
<212> TYPE: PRT
<213> ORGANISM: Homo sapiens

<400> SEQUENCE: 6

Met Ala Ser Gly Gln Gly Pro Gly Pro Pro Arg Gln Glu Cys Gly Glu
1               5                   10                  15

Pro Ala Leu Pro Ser Ala Ser Glu Glu Gln Val Ala Gln Asp Thr Glu
            20                  25                  30

Glu Val Phe Arg Ser Tyr Val Phe Tyr Arg His Gln Gln Glu Gln Glu
            35                  40                  45

Ala Glu Gly Val Ala Ala Pro Ala Asp Pro Glu Met Val Thr Leu Pro
        50                  55                  60

Leu Gln Pro Ser Ser Thr Met Gly Gln Val Gly Arg Gln Leu Ala Ile
65                  70                  75                  80

Ile Gly Asp Asp Ile Asn Arg Arg Tyr Asp Ser Glu Phe Gln Thr Met
                85                  90                  95

Leu Gln His Leu Gln Pro Thr Ala Glu Asn Ala Tyr Glu Tyr Phe Thr
            100                 105                 110

Lys Ile Ala Thr Ser Leu Phe Glu Ser Gly Ile Asn Trp Gly Arg Val
            115                 120                 125

Val Ala Leu Leu Gly Phe Gly Tyr Arg Leu Ala Leu His Val Tyr Gln
            130                 135                 140

His Gly Leu Thr Gly Phe Leu Gly Gln Val Thr Arg Phe Val Val Asp
145                 150                 155                 160

Phe Met Leu His His Cys Ile Ala Arg Trp Ile Ala Gln Arg Gly Gly
                165                 170                 175

Trp Val Ala Ala Leu Asn Leu Gly Asn Gly Pro Ile Leu Asn Val Leu
            180                 185                 190

Val Val Leu Gly Val Val Leu Leu Gly Gln Phe Val Val Arg Arg Phe
            195                 200                 205

Phe Lys Ser
    210

<210> SEQ ID NO 7
<211> LENGTH: 170
<212> TYPE: PRT
<213> ORGANISM: Homo sapiens

<400> SEQUENCE: 7

Met Ser Gln Ser Asn Arg Glu Leu Val Val Asp Phe Leu Ser Tyr Lys
1               5                   10                  15

Leu Ser Gln Lys Gly Tyr Ser Trp Ser Gln Phe Ser Asp Val Glu Glu
            20                  25                  30
```

```
Asn Arg Thr Glu Ala Pro Glu Gly Thr Glu Ser Glu Met Glu Thr Pro
            35                  40                  45

Ser Ala Ile Asn Gly Asn Pro Ser Trp His Leu Ala Asp Ser Pro Ala
        50                  55                  60

Val Asn Gly Ala Thr Gly His Ser Ser Ser Leu Asp Ala Arg Glu Val
65                  70                  75                  80

Ile Pro Met Ala Ala Val Lys Gln Ala Leu Arg Glu Ala Gly Asp Glu
                85                  90                  95

Phe Glu Leu Arg Tyr Arg Arg Ala Phe Ser Asp Leu Thr Ser Gln Leu
            100                 105                 110

His Ile Thr Pro Gly Thr Ala Tyr Gln Ser Phe Glu Gln Asp Thr Phe
        115                 120                 125

Val Glu Leu Tyr Gly Asn Asn Ala Ala Glu Ser Arg Lys Gly Gln
    130                 135                 140

Glu Arg Phe Asn Arg Trp Phe Leu Thr Gly Met Thr Val Ala Gly Val
145                 150                 155                 160

Val Leu Leu Gly Ser Leu Phe Ser Arg Lys
                165                 170

<210> SEQ ID NO 8
<211> LENGTH: 160
<212> TYPE: PRT
<213> ORGANISM: Homo sapiens

<400> SEQUENCE: 8

Met Ser Glu Val Arg Pro Leu Ser Arg Asp Ile Leu Met Glu Thr Leu
1               5                   10                  15

Leu Tyr Glu Gln Leu Leu Glu Pro Pro Thr Met Glu Val Leu Gly Met
            20                  25                  30

Thr Asp Ser Glu Glu Asp Leu Asp Pro Met Glu Asp Phe Asp Ser Leu
        35                  40                  45

Glu Cys Met Glu Gly Ser Asp Ala Leu Ala Leu Arg Leu Ala Cys Ile
    50                  55                  60

Gly Asp Glu Met Asp Val Ser Leu Arg Ala Pro Arg Leu Ala Gln Leu
65                  70                  75                  80

Ser Glu Val Ala Met His Ser Leu Gly Leu Ala Phe Ile Tyr Asp Gln
                85                  90                  95

Thr Glu Asp Ile Arg Asp Val Leu Arg Ser Phe Met Asp Gly Phe Thr
            100                 105                 110

Thr Leu Lys Glu Asn Ile Met Arg Phe Trp Arg Ser Pro Asn Pro Gly
        115                 120                 125

Ser Trp Val Ser Cys Glu Gln Val Leu Leu Ala Leu Leu Leu Leu Leu
    130                 135                 140

Ala Leu Leu Pro Leu Leu Ser Gly Gly Leu His Leu Leu Leu Lys
145                 150                 155                 160

<210> SEQ ID NO 9
<211> LENGTH: 218
<212> TYPE: PRT
<213> ORGANISM: Homo sapiens

<400> SEQUENCE: 9

Met Asp Gly Ser Gly Glu Gln Pro Arg Gly Gly Gly Pro Thr Ser Ser
1               5                   10                  15

Glu Gln Ile Met Lys Thr Gly Ala Leu Leu Leu Gln Gly Phe Ile Gln
            20                  25                  30
```

-continued

```
Asp Arg Ala Gly Arg Met Gly Gly Glu Ala Pro Glu Leu Ala Leu Asp
            35                  40                  45
Pro Val Pro Gln Asp Ala Ser Thr Lys Lys Leu Ser Glu Cys Leu Lys
 50                  55                  60
Arg Ile Gly Asp Glu Leu Asp Ser Asn Met Glu Leu Gln Arg Met Ile
65                  70                  75                  80
Ala Ala Val Asp Thr Asp Ser Pro Arg Glu Val Phe Phe Arg Val Ala
                85                  90                  95
Ala Asp Met Phe Ser Asp Gly Asn Phe Asn Trp Gly Arg Val Val Ala
            100                 105                 110
Leu Phe Tyr Phe Ala Ser Lys Leu Val Leu Lys Ala Leu Cys Thr Lys
            115                 120                 125
Val Pro Glu Leu Ile Arg Thr Ile Met Gly Trp Thr Leu Asp Phe Leu
130                 135                 140
Arg Glu Arg Leu Leu Gly Trp Ile Gln Asp Gln Gly Gly Trp Val Arg
145                 150                 155                 160
Leu Leu Lys Pro Pro His Pro His His Arg Ala Leu Thr Thr Ala Pro
                165                 170                 175
Ala Pro Pro Ser Leu Pro Pro Ala Thr Pro Leu Gly Pro Trp Ala Phe
                180                 185                 190
Trp Ser Arg Ser Gln Trp Cys Pro Leu Pro Ile Phe Arg Ser Ser Asp
            195                 200                 205
Val Val Tyr Asn Ala Phe Ser Leu Arg Val
            210                 215

<210> SEQ ID NO 10
<211> LENGTH: 239
<212> TYPE: PRT
<213> ORGANISM: Homo sapiens

<400> SEQUENCE: 10

Met Ala His Ala Gly Arg Thr Gly Tyr Asp Asn Arg Glu Ile Val Met
1               5                   10                  15
Lys Tyr Ile His Tyr Lys Leu Ser Gln Arg Gly Tyr Glu Trp Asp Ala
                20                  25                  30
Gly Asp Val Gly Ala Ala Pro Pro Gly Ala Ala Pro Ala Pro Gly Ile
            35                  40                  45
Phe Ser Ser Gln Pro Gly His Thr Pro His Pro Ala Ala Ser Arg Asp
 50                  55                  60
Pro Val Ala Arg Thr Ser Pro Leu Gln Thr Pro Ala Ala Pro Gly Ala
65                  70                  75                  80
Ala Ala Gly Pro Ala Leu Ser Pro Val Pro Pro Val Val His Leu Thr
                85                  90                  95
Leu Arg Gln Ala Gly Asp Asp Phe Ser Arg Arg Tyr Arg Arg Asp Phe
            100                 105                 110
Ala Glu Met Ser Ser Gln Leu His Leu Thr Pro Phe Thr Ala Arg Gly
            115                 120                 125
Arg Phe Ala Thr Val Val Glu Glu Leu Phe Arg Asp Gly Val Asn Trp
130                 135                 140
Gly Arg Ile Val Ala Phe Phe Glu Phe Gly Gly Val Met Cys Val Glu
145                 150                 155                 160
Ser Val Asn Arg Glu Met Ser Pro Leu Val Asp Asn Ile Ala Leu Trp
                165                 170                 175
Met Thr Glu Tyr Leu Asn Arg His Leu His Thr Trp Ile Gln Asp Asn
```

```
                   180                 185                 190
Gly Gly Trp Asp Ala Phe Val Glu Leu Tyr Gly Pro Ser Met Arg Pro
            195                 200                 205

Leu Phe Asp Phe Ser Trp Leu Ser Leu Lys Thr Leu Leu Ser Leu Ala
            210                 215                 220

Leu Val Gly Ala Cys Ile Thr Leu Gly Ala Tyr Leu Gly His Lys
225                 230                 235

<210> SEQ ID NO 11
<211> LENGTH: 205
<212> TYPE: PRT
<213> ORGANISM: Homo sapiens

<400> SEQUENCE: 11

Met Ala His Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Ala
            20                  25                  30

Gly Asp Val Gly Ala Ala Pro Pro Gly Ala Ala Pro Ala Pro Gly Ile
        35                  40                  45

Phe Ser Ser Gln Pro Gly His Thr Pro His Pro Ala Ala Ser Arg Asp
    50                  55                  60

Pro Val Ala Arg Thr Ser Pro Leu Gln Thr Pro Ala Ala Pro Gly Ala
65                  70                  75                  80

Ala Ala Gly Pro Ala Leu Ser Pro Val Pro Pro Val Val His Leu Ala
                85                  90                  95

Leu Arg Gln Ala Gly Asp Asp Phe Ser Arg Arg Tyr Arg Gly Asp Phe
            100                 105                 110

Ala Glu Met Ser Ser Gln Leu His Leu Thr Pro Phe Thr Ala Arg Gly
        115                 120                 125

Arg Phe Ala Thr Val Val Glu Glu Leu Phe Arg Asp Gly Val Asn Trp
    130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
            180                 185                 190

Gly Gly Trp Val Gly Ala Ser Gly Asp Val Ser Leu Gly
        195                 200                 205

<210> SEQ ID NO 12
<211> LENGTH: 345
<212> TYPE: PRT
<213> ORGANISM: Homo sapiens

<400> SEQUENCE: 12

Leu Ala Gln Arg Gly Gly Ala Arg Arg Pro Arg Gly Asp Arg Glu Arg
1               5                   10                  15

Leu Gly Ser Arg Leu Arg Ala Leu Arg Pro Gly Arg Glu Pro Arg Gln
            20                  25                  30

Ser Glu Pro Pro Ala Gln Arg Gly Pro Pro Ser Arg Arg Pro Pro
        35                  40                  45

Ala Arg Ser Thr Ala Ser Gly His Asp Arg Pro Thr Arg Gly Ala Ala
    50                  55                  60

Ala Gly Ala Arg Arg Pro Arg Met Lys Lys Lys Thr Arg Arg Arg Ser
```

```
                65                  70                  75                  80
Thr Arg Ser Glu Glu Leu Thr Arg Ser Glu Glu Leu Thr Leu Ser Glu
                    85                  90                  95
Glu Ala Thr Trp Ser Glu Glu Ala Thr Gln Ser Glu Glu Ala Thr Gln
                    100                 105                 110
Gly Glu Glu Met Asn Arg Ser Gln Glu Val Thr Arg Asp Glu Glu Ser
                    115                 120                 125
Thr Arg Ser Glu Glu Val Thr Arg Glu Glu Met Ala Ala Ala Gly Leu
                130                 135                 140
Thr Val Thr Val Thr His Ser Asn Glu Lys His Asp Leu His Val Thr
145                 150                 155                 160
Ser Gln Gln Gly Ser Ser Glu Pro Val Val Gln Asp Leu Ala Gln Val
                    165                 170                 175
Val Glu Glu Val Ile Gly Val Pro Gln Ser Phe Gln Lys Leu Ile Phe
                    180                 185                 190
Lys Gly Lys Ser Leu Lys Glu Met Glu Thr Pro Leu Ser Ala Leu Gly
                    195                 200                 205
Ile Gln Asp Gly Cys Arg Val Met Leu Ile Gly Lys Lys Asn Ser Pro
                    210                 215                 220
Gln Glu Glu Val Glu Leu Lys Lys Leu Lys His Leu Glu Lys Ser Val
225                 230                 235                 240
Glu Lys Ile Ala Asp Gln Leu Glu Glu Leu Asn Lys Glu Leu Thr Gly
                    245                 250                 255
Ile Gln Gln Gly Phe Leu Pro Lys Asp Leu Gln Ala Glu Ala Leu Cys
                    260                 265                 270
Lys Leu Asp Arg Arg Val Lys Ala Thr Ile Glu Gln Phe Met Lys Ile
                    275                 280                 285
Leu Glu Glu Ile Asp Thr Leu Ile Leu Pro Glu Asn Phe Lys Asp Ser
                290                 295                 300
Arg Leu Lys Arg Lys Gly Leu Val Lys Lys Val Gln Ala Phe Leu Ala
305                 310                 315                 320
Glu Cys Asp Thr Val Glu Gln Asn Ile Cys Gln Glu Thr Glu Arg Leu
                    325                 330                 335
Gln Ser Thr Asn Phe Ala Leu Ala Glu
                    340                 345

<210> SEQ ID NO 13
<211> LENGTH: 239
<212> TYPE: PRT
<213> ORGANISM: Homo sapiens

<400> SEQUENCE: 13

Met Ala His Ala Gly Arg Thr Gly Tyr Asp Asn Arg Glu Ile Val Met
1               5                   10                  15
Lys Tyr Ile His Tyr Lys Leu Ser Gln Arg Gly Tyr Glu Trp Asp Ala
                20                  25                  30
Gly Asp Val Gly Ala Ala Pro Pro Gly Ala Ala Pro Ala Pro Gly Ile
            35                  40                  45
Phe Ser Ser Gln Pro Gly His Thr Pro His Pro Ala Ala Ser Arg Asp
        50                  55                  60
Pro Val Ala Arg Thr Ser Pro Leu Gln Thr Pro Ala Ala Pro Gly Ala
65                  70                  75                  80
Ala Ala Gly Pro Ala Leu Ser Pro Val Pro Pro Val Val His Leu Thr
                    85                  90                  95
```

```
Leu Arg Gln Ala Gly Asp Asp Phe Ser Arg Arg Tyr Arg Arg Asp Phe
                100                 105                 110

Ala Glu Met Ser Ser Gln Leu His Leu Thr Pro Phe Thr Ala Arg Gly
            115                 120                 125

Arg Phe Ala Thr Val Val Glu Glu Leu Phe Arg Asp Gly Val Asn Trp
        130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
            180                 185                 190

Gly Gly Trp Asp Ala Phe Val Glu Leu Tyr Gly Pro Ser Met Arg Pro
        195                 200                 205

Leu Phe Asp Phe Ser Trp Leu Ser Leu Lys Thr Leu Leu Ser Leu Ala
    210                 215                 220

Leu Val Gly Ala Cys Ile Thr Leu Gly Ala Tyr Leu Gly His Lys
225                 230                 235

<210> SEQ ID NO 14
<211> LENGTH: 195
<212> TYPE: PRT
<213> ORGANISM: Homo sapiens

<400> SEQUENCE: 14

Met Asp Cys Glu Val Asn Asn Gly Ser Ser Leu Arg Asp Glu Cys Ile
1               5                   10                  15

Thr Asn Leu Leu Val Phe Gly Phe Leu Gln Ser Cys Ser Asp Asn Ser
            20                  25                  30

Phe Arg Arg Glu Leu Asp Ala Leu Gly His Glu Leu Pro Val Leu Ala
        35                  40                  45

Pro Gln Trp Glu Gly Tyr Asp Glu Leu Gln Thr Asp Gly Asn Arg Ser
    50                  55                  60

Ser His Ser Arg Leu Gly Arg Ile Glu Ala Asp Ser Glu Ser Gln Glu
65                  70                  75                  80

Asp Ile Ile Arg Asn Ile Ala Arg His Leu Ala Gln Val Gly Asp Ser
                85                  90                  95

Met Asp Arg Ser Ile Pro Pro Gly Leu Val Asn Gly Leu Ala Leu Gln
            100                 105                 110

Leu Arg Asn Thr Ser Arg Ser Glu Glu Asp Arg Asn Arg Asp Leu Ala
        115                 120                 125

Thr Ala Leu Glu Gln Leu Leu Gln Ala Tyr Pro Arg Asp Met Glu Lys
    130                 135                 140

Glu Lys Thr Met Leu Val Leu Ala Leu Leu Leu Ala Lys Lys Val Ala
145                 150                 155                 160

Ser His Thr Pro Ser Leu Leu Arg Asp Val Phe His Thr Thr Val Asn
                165                 170                 175

Phe Ile Asn Gln Asn Leu Arg Thr Tyr Val Arg Ser Leu Ala Arg Asn
            180                 185                 190

Gly Met Asp
        195

CEN0269 1
```

What is claimed is:

1. A protein expression enhancing Bcl2 related nucleic acid, comprising a first nucleic acid encoding at least one expressible protein and a second nucleic acid encoding at least one Bcl2 related protein, wherein expression of said expressible protein is enhanced by transcription or translation of said second nucleic acid.

2. A nucleic acid according to claim 1, wherein said expressible protein is an immunoglobulin protein or portion thereof.

3. A nucleic acid according to claim 2, wherein said immunoglobulin portion is selected from at least one complementarity determining region (CDR), at least one variable region, at least one light chain, at least one heavy chain, at least one Fab', at least one Fab'$_2$, or at least one CDR comprising portion thereof.

4. A nucleic acid comprising a protein expression enhancing Bcl2 related nucleic acid according to claim 1.

5. An expression vector comprising a nucleic acid according to claim 4, wherein said expression vector expresses said at least one expressible protein when provided or transcribed and translated in a host cell.

6. A host cell comprising a nucleic acid according to claim 4, wherein said nucleic acid expresses said at least one expressible protein when provided or transcribed and translated in a host cell.

7. A mammalian cell line comprising a transiently expressed nucleic acid according to claim 4.

8. A mammalian cell line comprising a nucleic acid according to claim 4 that has been integrated into the genomic DNA of the cells of said cell line.

9. A protein expressed from a cell line according to claim 7.

10. A protein expressed from a cell line according to claim 8.

11. A protein according to claim 9, wherein said protein is selected from a therapeutic protein or a diagnostic protein.

12. A protein according to claim 10, wherein said protein is selected from a therapeutic protein or a diagnostic protein.

13. A protein according to claim 11, wherein said protein is selected from an immunoglobulin, a soluble receptor, a transmembrane protein, a cytoplasmic protein, a soluble protein, an extracellular protein, or any fragment or portion thereof.

14. A protein according to claim 12, wherein said protein is selected from an immunoglobulin, a soluble receptor, a transmembrane protein, a cytoplasmic protein, a soluble protein, an extracellular protein, or any fragment or portion thereof.

15. A protein according to claim 13, wherein said immunoglobulin is selected from an IgG, an IgA, and an IgM.

16. A protein according to claim 14, wherein said immunoglobulin is selected from an IgG, an IgA, and an IgM.

17. A protein according to claim 15, wherein said IgG is selected from an IgG1, and IgG2, and IgG3 and an IgG4.

18. A protein according to claim 16, wherein said IgG is selected from an IgG1, and IgG2, and IgG3 and an IgG4.

19. A protein according to claim 17, wherein said immunoglobulin fragment or portion is at least one selected from a fab, a fab', a scFv, Fab'2 or a portion of an immunoglobulin comprising at least one CDR sequence.

20. A protein according to claim 18, wherein said immunoglobulin fragment or portion is at least one selected from a fab, a fab', a scFv, Fab'2 or a portion of an immunoglobulin comprising at least one CDR sequence.

21. A protein according to claim 13, wherein said immunoglobulin is selected from a rodent, a human, a chimeric, a humanized or a primate immunoglobulin or fragment thereof.

22. A protein according to claim 14, wherein said immunoglobulin is selected from a rodent, a human, a chimeric, a humanized or a primate immunoglobulin or fragment thereof.

23. A formulation comprising a protein according to claim 9.

24. A formulation comprising a protein according to claim 10.

25. A container, comprising a protein according to claim 9.

26. A container, comprising a protein according to claim 10.

27. A method for enhancing protein expression, comprising providing a host cell expressing a protein, wherein said host cell further transcribes or translates at least one Bcl2 related protein encoding nucleic acid, and wherein said host cell is recombinant or has been modified to turn on transcription of said protein or said Bcl2 related protein encoding nucleic acid.

28. A method according to claim 27, wherein culturing of said host cell requires less robust media that the culturing of said host cell without said transcription of said Bcl2 related protein encoding nucleic acid.

29. A protein expressed by a method according to claim 27.

30. A protein according to claim 29, wherein said protein is selected from a therapeutic protein or a diagnostic protein.

31. A protein according to claim 29, wherein said protein is selected from an immunoglobulin, a soluble receptor, a transmembrane protein, a cytoplasmic protein, a soluble protein, an extracellular protein, or any fragment or portion thereof.

32. A protein according to claim 31, wherein said immunoglobulin is selected from an IgG, an IgA, and an IgM.

33. A protein according to claim 32, wherein said IgG is selected from an IgG1, and IgG2, and IgG3 and an IgG4.

34. A protein according to claim 31, wherein said immunoglobulin fragment or portion is at least one selected from a fab, a fab', a scFv, Fab'2 or a portion of an immunoglobulin comprising at least one CDR sequence.

35. A protein according to claim 31, wherein said immunoglobulin is selected from a rodent, a human, a chimeric, a humanized or a primate immunoglobulin or fragment thereof.

36. A formulation comprising a protein according to claim 29.

37. A container, comprising a protein according to claim 29.

* * * * *